(12) United States Patent
Kato

(10) Patent No.: US 8,172,839 B2
(45) Date of Patent: May 8, 2012

(54) PFO CLOSING DEVICE

(75) Inventor: Yukitoshi Kato, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 888 days.

(21) Appl. No.: 12/230,090

(22) Filed: Aug. 22, 2008

(65) Prior Publication Data
US 2009/0005780 A1 Jan. 1, 2009

Related U.S. Application Data

(63) Continuation of application No. PCT/JP2007/053977, filed on Feb. 23, 2007.

(30) Foreign Application Priority Data

Feb. 24, 2006 (JP) .................................. 2006-047636

(51) Int. Cl.
*A61B 18/18* (2006.01)

(52) U.S. Cl. ........................................... 606/50; 606/215

(58) Field of Classification Search .................... 606/50, 606/215, 151, 2, 21, 27, 32
See application file for complete search history.

(56) References Cited

U.S. PATENT DOCUMENTS

| | | | |
|---|---|---|---|
| 5,507,744 A | 4/1996 | Tay et al. | |
| 5,709,224 A | 1/1998 | Behl et al. | |
| 5,810,810 A | 9/1998 | Tay et al. | |
| 5,827,268 A | 10/1998 | Laufer | |
| 5,919,200 A | 7/1999 | Stambaugh et al. | |
| 6,004,316 A | 12/1999 | Laufer | |
| 6,063,085 A | 5/2000 | Tay et al. | |
| 6,077,261 A | 6/2000 | Behl et al. | |
| 6,102,926 A | 8/2000 | Tartaglia et al. | |
| 6,629,534 B1 | 10/2003 | St. Goar et al. | |
| 6,752,813 B2 | 6/2004 | Goldfarb et al. | |
| 6,939,348 B2 | 9/2005 | Malecki et al. | |
| 7,165,552 B2 | 1/2007 | Deem et al. | |
| 7,186,251 B2 | 3/2007 | Malecki et al. | |
| 7,226,467 B2 | 6/2007 | Lucatero et al. | |

(Continued)

FOREIGN PATENT DOCUMENTS

WO WO 2004/086944 A2 10/2004
(Continued)

OTHER PUBLICATIONS

European Office Action in corresponding application No. 07 715 127.2-1265 dated Feb. 6, 2009.

*Primary Examiner* — Jackie Ho
*Assistant Examiner* — Brandy C Scott
(74) *Attorney, Agent, or Firm* — Buchanan Ingersoll & Rooney PC

(57) ABSTRACT

A PFO closing device for bringing the septum primum and the septum secundum into contact with each other and joining them together includes a clamping mechanism and energy supplying device. The clamping mechanism includes a needle part for puncturing the septum primum, and a clamping member for cooperating with the needle part in clamping therebetween tissue of the septum primum and the septum secundum. The energy supplying device supplies energy for joining the tissues clamped by the needle part and the clamping member. The clamping mechanism is mounted in a catheter so as to be protrudable from and retractable into the catheter.

10 Claims, 19 Drawing Sheets

U.S. PATENT DOCUMENTS

| | | |
|---|---|---|
| 7,257,450 B2 | 8/2007 | Auth et al. |
| 7,293,562 B2 | 11/2007 | Malecki et al. |
| 7,311,701 B2 | 12/2007 | Gifford et al. |
| 2003/0144652 A1 | 7/2003 | Baker et al. |
| 2004/0003819 A1 | 1/2004 | St. Goar et al. |
| 2004/0030382 A1 | 2/2004 | St. Goar et al. |
| 2004/0039442 A1 | 2/2004 | St. Goar et al. |
| 2004/0044350 A1 | 3/2004 | Martin et al. |
| 2004/0049207 A1 | 3/2004 | Goldfarb et al. |
| 2004/0068274 A1 | 4/2004 | Hooven |
| 2004/0092962 A1 | 5/2004 | Thornton et al. |
| 2004/0225300 A1 | 11/2004 | Goldfarb et al. |
| 2004/0230185 A1* | 11/2004 | Malecki et al. .................. 606/2 |
| 2004/0243122 A1 | 12/2004 | Auth et al. |
| 2004/0267191 A1 | 12/2004 | Gifford, III et al. |
| 2005/0021056 A1 | 1/2005 | St. Goar et al. |
| 2005/0021057 A1 | 1/2005 | St. Goar et al. |
| 2005/0033288 A1 | 2/2005 | Auth et al. |
| 2005/0033446 A1 | 2/2005 | Deem et al. |
| 2005/0080406 A1 | 4/2005 | Malecki et al. |
| 2005/0131401 A1 | 6/2005 | Malecki et al. |
| 2005/0131460 A1 | 6/2005 | Gifford, III et al. |
| 2005/0192626 A1 | 9/2005 | Widomski et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2006/0020275 A1 | 1/2006 | Goldfarb et al. |
| 2006/0027241 A1 | 2/2006 | Malecki et al. |
| 2006/0074410 A1 | 4/2006 | Malecki et al. |
| 2006/0241581 A1 | 10/2006 | Malecki et al. |
| 2006/0241582 A1 | 10/2006 | Malecki et al. |
| 2006/0241583 A1 | 10/2006 | Malecki et al. |
| 2006/0241584 A1 | 10/2006 | Malecki et al. |
| 2006/0247612 A1 | 11/2006 | Malecki et al. |
| 2006/0271030 A1 | 11/2006 | Francis et al. |
| 2006/0271040 A1 | 11/2006 | Horne et al. |
| 2006/0271089 A1 | 11/2006 | Alejandro et al. |
| 2006/0276779 A1 | 12/2006 | Malecki et al. |
| 2006/0276846 A1 | 12/2006 | Malecki et al. |
| 2007/0010806 A1 | 1/2007 | Malecki et al. |
| 2007/0027445 A1 | 2/2007 | Gifford et al. |
| 2007/0038293 A1 | 2/2007 | St.Goar et al. |
| 2007/0044811 A1 | 3/2007 | Deem et al. |
| 2007/0078485 A1 | 4/2007 | Deem et al. |
| 2007/0088355 A9 | 4/2007 | Auth et al. |
| 2007/0093804 A1 | 4/2007 | Kaveckis et al. |
| 2007/0093805 A1 | 4/2007 | Auth et al. |
| 2007/0100324 A1 | 5/2007 | Tempel et al. |
| 2007/0100356 A1 | 5/2007 | Lucatero et al. |
| 2007/0106214 A1 | 5/2007 | Gray et al. |
| 2007/0112347 A1 | 5/2007 | Malecki et al. |
| 2007/0118155 A1 | 5/2007 | Goldfarb et al. |
| 2007/0123824 A1 | 5/2007 | Kaveckis |
| 2007/0123851 A1 | 5/2007 | Alejandro et al. |
| 2007/0123852 A1 | 5/2007 | Deem et al. |
| 2007/0129737 A1* | 6/2007 | Goldfarb et al. .............. 606/151 |
| 2007/0203479 A1 | 8/2007 | Auth et al. |
| 2007/0287999 A1 | 12/2007 | Malecki et al. |
| 2007/0299434 A1 | 12/2007 | Malecki et al. |
| 2008/0004658 A1 | 1/2008 | Malecki et al. |
| 2008/0009859 A1 | 1/2008 | Auth et al. |
| 2008/0051703 A1 | 2/2008 | Thornton et al. |
| 2008/0051807 A1 | 2/2008 | St. Goar et al. |
| 2008/0058683 A1 | 3/2008 | Gifford et al. |
| 2008/0097489 A1 | 4/2008 | Goldfarb et al. |
| 2008/0140064 A1 | 6/2008 | Vegesna |
| 2008/0140068 A1 | 6/2008 | Taimisto |
| 2008/0140069 A1 | 6/2008 | Filloux et al. |
| 2008/0140070 A1 | 6/2008 | Filloux et al. |
| 2008/0140071 A1 | 6/2008 | Vegesna |
| 2008/0140074 A1 | 6/2008 | Horne et al. |
| 2008/0140112 A1 | 6/2008 | Horne |
| 2008/0140113 A1 | 6/2008 | Taimisto et al. |
| 2008/0140170 A1 | 6/2008 | Filloux et al. |

FOREIGN PATENT DOCUMENTS

| | | | |
|---|---|---|---|
| WO | WO 2004/103162 A2 | 12/2004 | |
| WO | WO 2006/110830 A2 | 10/2006 | |

* cited by examiner

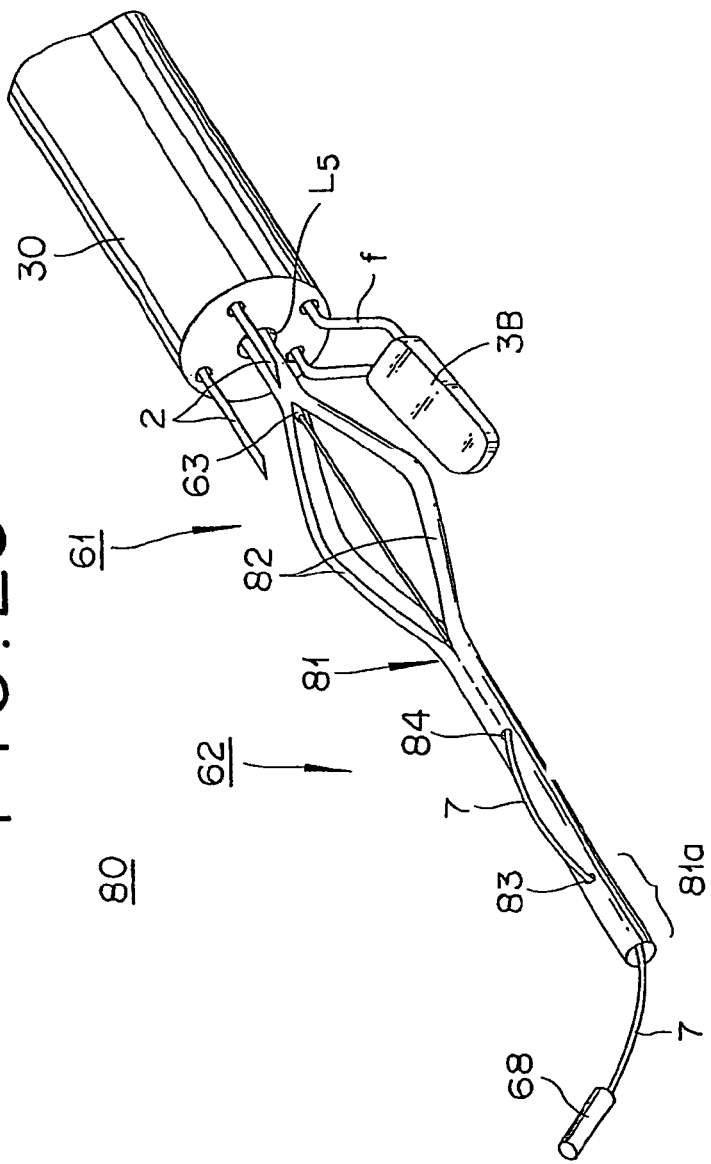

PFO CLOSING DEVICE

This application is a continuation of, and claims priority under 35 U.S.C. §120 to, International Application No. PCT/JP2007/053977 filed on Feb. 23, 2007. This application also claims priority under 35 U.S.C. §119(a) to Japanese Application No. 2006-047636 filed on Feb. 24, 2006, the entire content of both of which is incorporated herein by reference.

TECHNOLOGICAL FIELD

The present invention generally relates to a medical device. More specifically, the invention pertains to a patent foramen ovale (PFO) closing device for closing a PFO in a person's heart.

BACKGROUND DISCUSSION

Recently, patent foramen ovale (hereinafter referred to as PFO) has been identified as a cardiac factor in strokes and migraines. The PFO is a symptom in which the oval foramen (foramen ovale) for shortcircuiting blood between the left and right sides in the heart in the fetal period of a person's life remains even after the person has gown up. It is said that 20-30% of grown-up people have this disease.

The PFO is generated in the septum secundum (hereinafter referred to as SP) of a heart. In a heart at normal time, the blood pressure in the left atrium of heart is higher than that in the right atrium of heart, so that the oval foramen is closed with the septum primum (hereinafter referred to as SP). However, when the blood pressure in the right atrium of the heart exceeds that in the left atrium of heart in certain circumstances (for example, at the time of coughing or straddling), the SP opens to the side of the left atrium of heart, resulting in blood flow from the side of the right atrium of heart (the vein side) to the side of the left atrium of heart (the artery side). If thrombi are contained in the blood in this case, the thrombi are transferred from the vein side to the artery side, and flow from the left atrium of heart into the left ventricle, then into the aorta and into the brain, possibly causing a stroke or migraine.

Examples of the treatment of such a disease include pharmacotherapy (aspirin, warfarin, or the like), closure of the PFO by percutaneous catheterization, and open heart surgery by extracorporeal circulation. Pharmacotherapy is the treatment which should be selected first, but it can be difficult to manage the dosage, and bleeding may not cease easily during the dosage. Percutaneous catheterization and the open heart surgery are radical treatments and remove the fear of recurrence, though they are invasive procedures. At the present stage, of these closure procedures, open heart surgery is more assured. However, taking into account the risk attendant on the extracorporeal circulation and the magnitude of the invasion attendant on skin incision, the treatment by percutaneous catheterization is more desirable, if it produces the same effect as that of the open heart surgery.

Devices for closure by use of percutaneous catheterization can be used also in the cases of closing a defect, such as cogenital atrial septal defect (ASD), PFO, ventricular septal defect (VSD), patent ductus arteriosus (PDA), etc. The conventional devices, however, are based on clamping the SP and the SS by use of a disk-like membrane or anchor member for closing the defect, and they are left indwelling in the patient's body.

The membrane and the anchor member are foreign matters for the body, and thrombi are liable to deposit thereon. Particularly, when a thrombus deposits on the disk-like membrane on the side of the left atrium of the heart, it may flow downstream to cause stroke, or may break the SP which is small in wall thickness. In addition, these members may be positionally deviated, instead of being positionally fixed in the state of clamping the relevant tissues.

In view of these points, recently, there has been proposed the PFO closing device as described in WO2004/086944 A2 (refer to Abstract, FIG. 10, etc.).

In use of this PFO closing device, the appliance is passed through the PFO from the right atrium of heart toward the left atrium of heart, the SP is drawn to the PFO to close the latter, and energy is applied thereto so as to join the tissues to each other.

SUMMARY

A patent foramen oval (PFO) closing device for bringing the septum primum and the septum secundum into contact with each other and joining them together comprises a catheter dimensioned to be positioned in a living body and advanced into an atrium of a heart, a needle part slidably positioned inside the catheter for puncturing the septum primum, a clamping member mounted on the catheter and cooperable with the needle part to clamp, between the clamping member and the needle part, tissue of the septum primum and the septum secundum, and an energy supplying means operatively connected to at least one of the needle part and the clamping member for supplying energy to join the tissue clamped between the needle part and the clamping member. The PFO closing device posses a relatively simple configuration, yet allows the SP and the SS to be reliably joined to each other through a relatively easy procedure, without leaving any foreign matter indwelling in the patient's body.

The PFO closing device posses a relatively simple configuration, yet allows the SP and the SS to be reliably joined to each other through a relatively easy procedure, without leaving any foreign matter indwelling in the patient's body.

According to another aspect, a PFO closing therapeutic method involves positioning a needle part at a central portion of a PFO, holding the SP (septum primum) so as to be non-retractable relative to the puncturing direction of the needle part, puncturing the SP with a needle, bringing the SP and the SS into contact with each other by clamping with the needle part and a clamping member, and passing an electric current in the needle part and the clamping member to thereby join the SP and the SS to each other.

The PFO closing device is wholly mounted in the catheter so as to be protrudable and retractable, so that by feeding the PFO closing device in the state of being retracted into the catheter, the device can be fed to a diseased (affected) part comparatively easily. In the case of the procedure, also, since the tissues are clamped in the condition where the needle part has punctured the SP, the SP and the SS can be relatively easily clamped, irrespective of the variety in the forms of them. Particularly where the part to be fused is set at the entrance of the PFO as viewed from the side of the right atrium of heart and the SP is punctured by the needle part, the tissues can be assuredly joined to each other, without any influence of the degree of overlap of the membranes, the thickness and shape of the membranes, or the like arising from the individual differences in the shape of the SP.

In the case of clamping the tissue by the needle part and the clamping member, the tissues are clamped elastically (springy). Therefore, a press bonding force which follows up to the tissues shrunk by heating can be exerted in a relatively sustained manner so that the adhesion factors such as melted collagen and elastin can be press bonded in a desired shape.

Since a relatively small-diameter and substantially rectilinear needle part is used as an electrode on one side of the clamping means, the tissues composed of the SP and the SS can be joined to each other without forming any hole greater than the needle-punctured hole, so that leakage of blood can be minimized.

Since substantially the needle part and the clamping member or both of them together with holding means are only stored in the catheter, the present device is simple in configuration, which facilitates the procedure.

The present device, when having the holding means, holds the tissues composed of the SP and the SS at the time of puncturing. Therefore, the puncturing operation or the joining operation can be performed accurately and assuredly, whereby the procedure can be made to be accurate, speedy and easy.

Particularly where the present device has holding means including a positioning part for positioning the needle part relative to the PFO and a holding part for holding the SP so that the SP cannot be retracted relative to the needle part, the operation of positioning the needle part and the operation of holding the SP can be carried out in an undivided manner. Therefore, even a thin-walled SP can be punctured at a predetermined position, without breakage or damage. This enhances largely the safety and easiness of the procedure, and the procedure can be carried out accurately and speedily. Particularly, the positioning and holding means ensures that the positioning of the needle part and the holding of the SP can be performed by only operating the operating member to move axially forwards or rearwards, so that the convenience or facility of the procedure is enhanced.

Preferably, the positioning and holding means has a main tube passed through the catheter and capable of being operated externally, an operating member provided in the main tube so as to be movable axially forwards and rearwards, is protruded from the distal end of the main tube, an intermediate sleeve body and a tip sleeve body are provided coaxially with the operating member, and a contact member brought into contact with the tip sleeve body by pulling the operating member is provided at a distal end portion of the operating member. The tip sleeve body and the intermediate sleeve body are connected to each other by a first elastic wire member, and the intermediate sleeve body and the tip sleeve body are connected to each other by a second elastic wire member deformable more easily than the first elastic wire member. The second elastic wire member is curved outwards by pulling the operating member to thereby function as the positioning part making springy contact with the inner edge of the PFO. The first elastic wire member between the tip sleeve body and the contact member and the intermediate sleeve body is curved by further pulling the operating member to thereby function as a holding part for holding the SP by the tip sleeve body and the contact member. This configuration helps ensure that the positioning and the holding of the SP can be performed more assuredly, thereby enhancing the safety, facility, accurateness, and speediness of the procedure. Preferably, the positioning and holding means has a structure in which a main tube capable of being, operated externally protrudes from the distal end of the catheter, an operating member movable axially forwards and rearwards is provided in the main tube, and an elastic second sleeve body is disposed at a distal end portion of the main tube. A positioning piece formed at a proximal portion of the second sleeve body is curved outwards by pulling, by the operating member, the second sleeve body protruded from the main tube, to thereby function as the positioning part making springy contact with the inner edge of the PFO, and a distal end portion of the second sleeve body is curved by further pulling the operating member to thereby function as a holding part for holding the SP from the side of the left atrium of heart. This ensures not only the safety, facility, accurateness, and speediness of the procedure but also a simpler configuration of the PFO closing device.

Preferably, the positioning and holding means has a positioning part including a pair of elastic wire members protruding from a distal end portion of the catheter so as to be opened wider, and a holding part for holding the SP in a non-retractable manner by a projected part formed at the center of an M shape into which distal end portions of the elastic wire members are deformed. This helps ensure not only the safety, facility, accurateness, and speediness of the procedure but also a simpler configuration of the PFO closing device and inexpensiveness of the device.

The positioning and holding means has a main tube passing through the catheter and capable of being operated externally, an operating member provided in the main tube so as to be movable axially forwards and rearwards is protruded from the distal end of the main tube, an intermediate sleeve body and a tip sleeve body are provided coaxially with the operating member, and a contact member brought into contact with the tip sleeve body by pulling the operating member is provided at a distal end portion of the operating member; the main tube and the intermediate sleeve body—are connected to each other by a first elastic wire member, the intermediate sleeve body and the tip sleeve body are connected to each other by a second elastic wire member and a third elastic wire member projectingly deformable more easily than the second elastic wire member; the first elastic wire member is curved outwards by pulling the operating member to thereby function as the positioning part making springy contact with the inner edge of the foramen ovale, and by further pulling the operating member, the second elastic wire member is curved so that the tip sleeve body and the contact member function as a holding part for holding the septum primum, and the third elastic wire member is curved outwards to thereby function as a crease smoothing part for smoothing out creases present in the septum primum. This also ensures not only the safety, facility, accurateness, and speediness of the procedure but also a simpler configuration of the PFO closing device.

BRIEF DESCRIPTION OF THE DRAWINGS

FIG. 29 is a schematic perspective view of a sixth embodiment of the PFO closing device disclosed herein.

DETAILED DESCRIPTION

Figure 1:
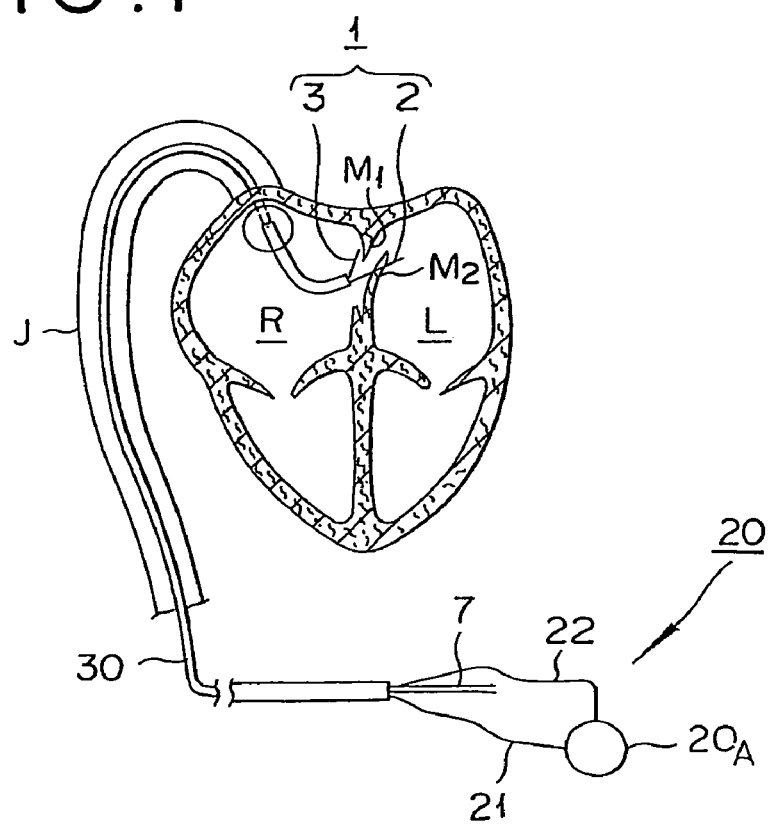
FIG. 1 is a schematic cross-sectional view showing the use of a first embodiment of the PFO closing device disclosed herein.

A first embodiment of the PFO closing device disclosed here is described with reference to FIGS. 1-3. As shown in FIG. 1, the PFO closing device according to this embodiment generally includes clamping means 1 for clamping a septum primum (hereinafter referred to as SP M2) and a septum secundum (hereinafter referred to as SS M1), and energy-supplying means 20 for supplying energy to join the tissues clamped by the clamping means 1. The clamping means 1 is movably positioned in the distal end (tip) of an elongated member 30, which includes a lumen, in a manner allowing the clamping means 1 to protrude out of and retract into (e.g., be movable forward and rearward) the elongated member. In the illustrated embodiment, the elongated hollow member (elongated lumen-possessing member) is a percutaneous catheter 30. In use, the clamping means 1, while being wholly stored or positioned in the catheter 30, is inserted in an inferior vena cava J. Then, in performing the procedure, the clamping means 1 protrudes from the distal end of the catheter 30, and the tissues of the SS M1 and the SP M2 of a heart in which a defect 0 (FIG. 4) of Patent Foramen Ovale (hereinafter referred to also as PFO 0) exists are clamped. In this condition, the tissues are joined by the energy supplied to the clamping means 1, whereby the defect 0 is closed.

Figure 2:
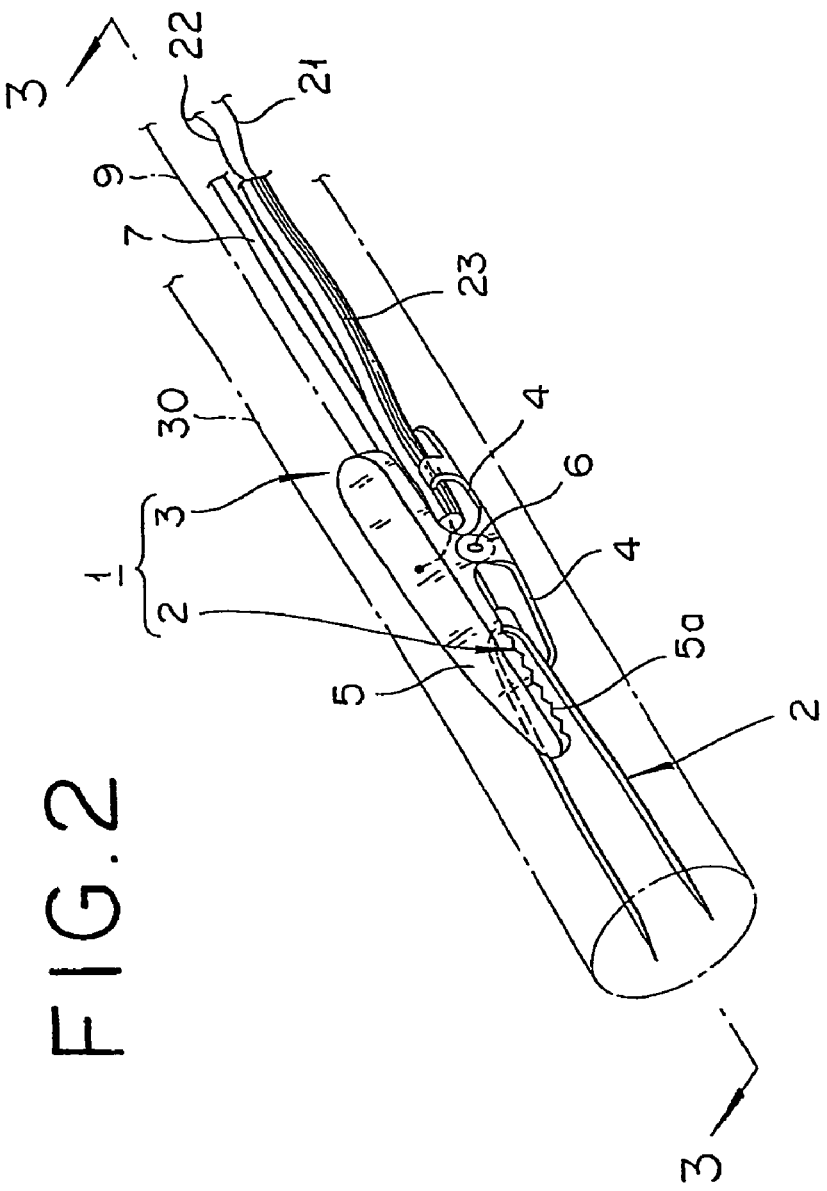
FIG. 2 is an enlarged perspective view of a part of the device according to the first embodiment.
Figure 3:
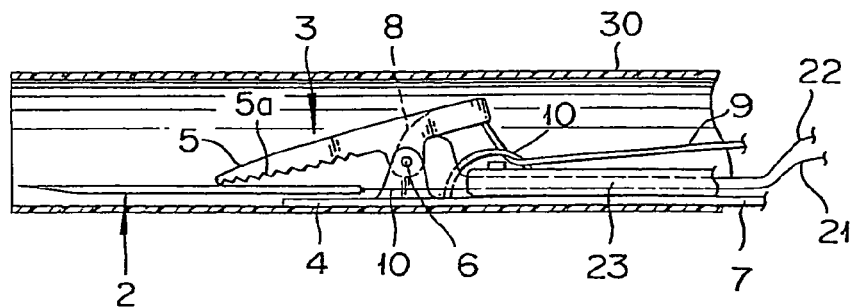
FIG. 3 is a cross-sectional view of the device taken along the section line 3-3 in FIG. 2.

More specifically, as shown in FIGS. 1-3, the clamping means 1 in this embodiment is a forceps-like clip composed of a needle part 2 for puncturing the SP M2 tissue, and a clamping member 3 cooperating with the needle part 2 to clamp the tissues composed of the SS M1 and the SP M2.

In this illustrated embodiment, the needle part 2 is comprised of two pointed wire members fixedly attached to a distal end portion of a first plate 4. The clamping member 3 includes a second plate 5, and the first plate 4 and the second plate 5 are moved to open and close, with a base shaft 6 as a center. An operating member 7 is attached to the proximal (rear) end side of the first plate 4, and the entire clamping means 1 is moved forwards and rearwards in the catheter 30 by moving the operating member 7 forwards and rearwards. The gripping force between the needle part 2 and the clamping member 3 is generated by an urging member (urging means) 8 seen in FIG. 3 provided between the first plate 4 and the second plate 5 which applies an urging force. In the illustrated embodiment, the urging member is in the form of a spring provided between the first plate 4 and the second plate 5.

The operating member 7, which can be composed of a comparatively stiff wire member, need not necessarily be connected to the needle part 2 side, and may instead be connected to the clamping member 3. The operating member 7 may be of any desired construction allowing it to move the clamping means 1 forwards and rearwards inside the catheter 30. By way of example, a wire of stainless steel, an Ni—Ti alloy, titanium, or the like can be used as the operating member 7.

In this embodiment, as shown in FIG. 2, the needle part 2 for puncturing the SP M2 is comprised of two sharp-pointed extremely-small-diameter wire members disposed in spaced apart relation to one another. When the SP M2 is punctured by such a needle part 2, the SP and the SS can be easily clamped, irrespective of their shapes. The needle part 2 (i.e., the pointed members forming the needle part 2) need not necessarily be solid, and may be hollow or annular. The outside diameter of each of the pointed members forming the needle part 2 is preferably in the range of 0.1 to 2 mm, for mounting it in the catheter 30. The material forming the needle part 2 is ordinarily SUS. However, other materials which do not exert bad influence on living bodies, such as gold, silver, platinum, tungsten, palladium, titanium, and alloys thereof can also be used. The spacing (interval) between the two members forming the needle parts 2 is not particularly limited, and may be in a certain range such that the SP M2 and the SS M1 can be clamped. In addition, the number of members forming the needle part 2 is not limited to two, and may be more.

The clamping member 3 may be a wholly flat plate-like member having a predetermined width so that it can cooperate with the pointed members of the needle part 2 in clamping the tissues of the SS M1 and the SP M2 therebetween. In this embodiment, to prevent slip-off or displacement and achieve secure gripping, the clamping member 3 is preferably provided with a rugged surface or rugged part 5a (roughened or knurled surface) on the clamping face side (the side facing the needle part 2). A traction wire 9 is connected to the proximal (rear) end of the clamping member 3 so that when the traction wire 9 is pulled axially rearwards, the clamping member 3 is moved away from the needle part 2 (i.e., moved towards an open position), with the base shaft 6 as a center, against the elasticity of the urging means 8. When the traction is relaxed, the clamping member 3 is closed toward the needle part 2 by the elasticity of the urging means 8 to achieve gripping. The traction wire 9 preferably has a structure, as for example shown in FIG. 3, in which a looped hook member 10 is provided at the proximal end of the first plate 4, and the traction wire 9 is extended to pass through the looped hook member 10, whereby the clamping member 3 can be relatively smoothly opened and closed relative to the needle part 2.

In this embodiment, the energy supplying means 20 is composed of an electricity supplying unit 2OA for melting the SP M2 and the SS M1 electrothermally and press bonding with an adhesion factor such as collagen and elastin. Particularly, in the case of clamping by the needle part 2 and the clamping member 3, the elasticity of the urging means 8 is constantly applied during clamping. Therefore, it is possible to apply, in a sustained manner, a press bonding force which follows up to the tissues thermally contracted, and to press bond the adhesion factor such as collagen and elastin in a desired shape.

For example, one end of one lead wire 21 is connected to the proximal end of the needle parts 2, and one end of the other lead wire 22 is connected to the proximal end of the clamping member 3. The other ends of these lead wires 21, 22 are contained in an insulating tube 23, are guided through the catheter 30 to the exterior, and are connected to the electricity supplying unit 2OA. The electricity supplying unit 2OA is composed of a power supply, a control unit for controlling the current, etc., and it has a known system configuration, the description of which is omitted here. The power supply may not necessarily be a DC power supply, and may be an AC power supply.

The energy supplying means 20 is not limited to an electrical power supply as described, but may be any one that can supply an energy capable of mutually joining the SP M2 and the SS M1 clamped by the clamping means 1. For example, ultrasonic wave, laser, microwave, or high-frequency wave can be used as a source of energy. In addition, as the energy supply system, there can be used a monopolar system in which an electric current is passed between the needle part 2 or the clamping member 3 on the side of the right atrium of heart R and a counter-electrode plate provided on the back side, a bipolar system in which an electric current is passed between the clamping member 3 on the side of the right atrium of heart R and the needle part 2 on the side of the left atrium of heart L, or the like system. Where a bipolar system, in which an electric current is controlled according to the impedance of the tissues between the needle part 2 and the clamping member 3, is used as the energy supplying means 20, it is possible to relatively easily cope with the conditions of the tissues of the SP M2 and the SS M1, which differ from patient to patient, and it is possible to obtain safety and facility of the procedure.

In this embodiment, the clamping means 1 is clip-like in form, and sliding friction may be generated between itself and the catheter 30, so that the needle parts 2 and the like are not liable to slip inside the catheter 30. In view of this, positioning means 40 (described later) for positioning the needle part 2 at a predetermined position relative to the PFO 0 is not provided here. However, such positioning means 40 may be provided if desired.

Now, the operations involving the use of this embodiment are described below.

Figure 4:
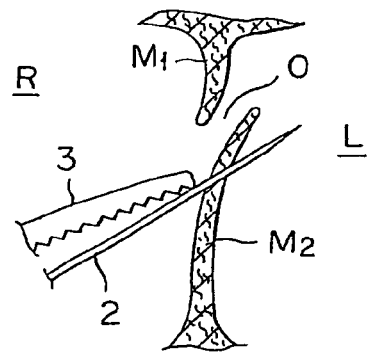
FIG. 4 is a cross-sectional view showing the condition where a needle part is protruded from a catheter.
Figure 5:
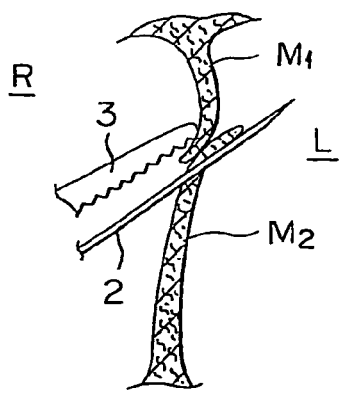
FIG. 5 is a cross-sectional view showing the condition where tissues are gripped between the needle part and the gripping member of the device.

FIG. 4 illustrates a condition in which the needle part protrudes from the catheter, and FIG. 5 illustrates a condition where the tissues are gripped between the needle part and the gripping member. First, the operator inserts a guide wire into a patient's body, then passes or advances a guiding catheter while using the guide wire as a guide. The guiding catheter is brought forwards to the right atrium of the heart R. When the distal end of the guide wire reaches the position of the PFO (O) of the heart and the guiding catheter has reached a position immediately before the PFO position, the position is maintained. Where a radiopaque material (for example, gold, silver, platinum, tungsten, palladium, or alloys thereof) is provided as a so-called marker at, for example, the distal end of the guide wire, the catheter member 13 can be inserted while confirming the position thereof by irradiation with X-rays or the like, and the position in the patient's body can be relatively accurately determined.

Using as a guide the guide wire preliminarily located at the position of the PFO, the catheter 30 with the needle part 2 and the clamping means 1 positioned or stored therein is inserted through the inferior vena cava J into the patient's body, as shown in FIGS. 2 and 3. Though the catheter 30 is relatively small in diameter and flexible as a whole, it can be relatively easily inserted when the stiffer guide wire is used as a guide. When the distal end of the catheter 30 protrudes from (distally beyond) the distal end of the guiding catheter and has reached the position of the PFO, the guide wire is evulsed or removed.

Subsequently, by operating the operating member 7, the needle parts 2 and the clamping member 3 for clamping protrude from the catheter 30. Then, as shown in FIG. 4, by operating the operating member 7, the needle part 2 protruding relative to the clamping means 3 is operated to puncture the SP M2 in the vicinity of the PFO 0.

In this condition, the traction wire 9 is pulled axially rearwards (proximally), and both the clamping member 3 and the needle part 2 are opened against the urging means 8 (so that the clamping member 3 and needle part relatively move away from each other), with the base shaft 6 as a center, upon which the clamping member 3 is opened wider from the needle part 2. In this way, the SS M1 and the SP M2 can be clamped in a mutually overlapping state between the clamping member 3 and the needle part 2. In this clamping condition, the pulling force acting on the traction wire 9 is removed, upon which the SS M1 and the SP M2 positioned in an overlapping manner between the clamping member 3 and the needle part 2 as shown in FIG. 5 are pressed in a sustained manner by the urging force of the urging member 8 (i.e., the spring or biasing force of the urging means).

Then, the electricity supplying unit 2OA is controlled to supply a predetermined current through the lead wires 21, 22, whereby the current is passed between the clamping member 3 and the needle part 2, and both tissues of the SS M1 and the SP M2 are heated. While applying the press bonding force which follows up to the tissues contracted by the heating, the adhesion factor such as collagen and elastin thus melted is press bonded in a desired shape.

When the tissues are fused to each other, the passage of current is stopped, the traction wire 9 is pulled to move the clamping member 3 away from the tissues, and the needle part 2 is evulsed from the SP M2. Though extremely tiny holes are left in the SP M2 after evulsion of the needle parts 2, they are relatively easily cured (healed) thereafter. Therefore, there is virtually no possibility of generation of thrombi or the like.

Then, the operating member 7 is operated to store or position the clamping means into the catheter 30 through the distal end of the latter, and the catheter 30 as a whole is evulsed or removed from the patient's body.

A second embodiment of the PFO closing device is illustrated in FIGS. 6-9. In the description which follows, features of the second embodiment of the closing device which are the same as those associated with the first embodiment are identified by the same reference numeral, and a detailed description of such features is not repeated.

The PFO closing device according to this second embodiment is preferable from the standpoint that the clamping means 1 can be stored or positioned in a catheter 30 in a more compact manner.

Figure 6:
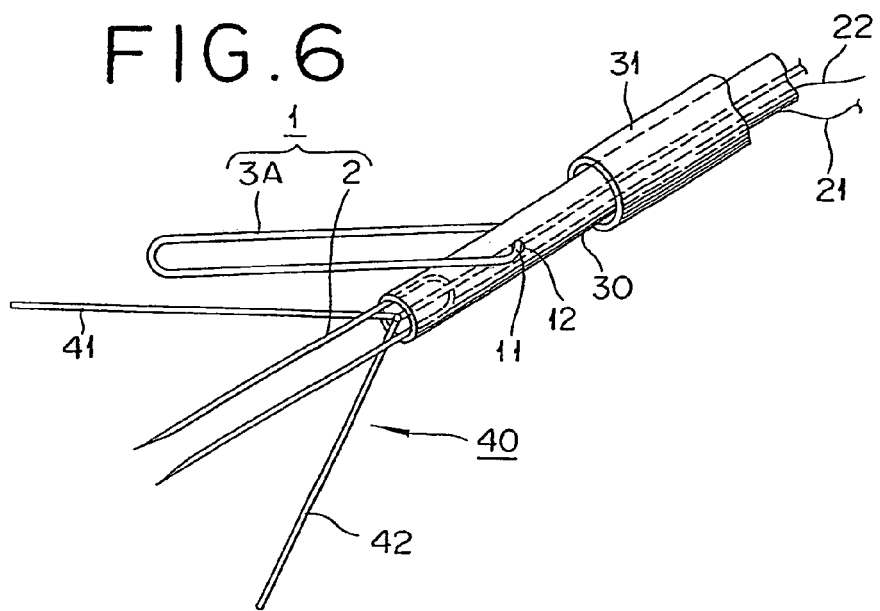
FIG. 6 is a schematic perspective view of a second embodiment of the PFO closing device disclosed herein.

As shown in FIG. 6, the PFO closing device in this embodiment generally includes a guiding catheter 31, the catheter 30, the clamping means 1, positioning means 40, and energy supplying means similar to the energy supply means of the first embodiment. The guiding catheter 31 is provided at an outermost portion of the device. The catheter 30 is positioned in the guiding catheter 31. The clamping means 1 includes the needle part 2 positionally fixedly provided inside the catheter 30 to protrude from the distal end of the catheter 30, and a clamping member 3A turnably provided in the outside of the distal end portion of the catheter 30. The positioning means 40 is for positioning the needle part 2 at the center of the PFO 0.

Figure 7:
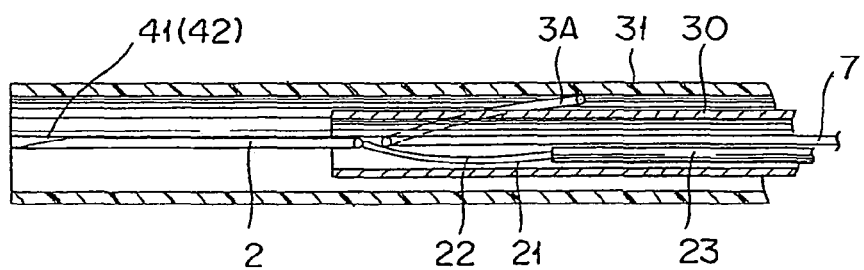
FIG. 7 is an enlarged cross-sectional view of a part of the device illustrated in FIG. 5, showing the stored condition of the PFO closing device according to the second embodiment.

As shown in FIG. 7, the needle part 2 constituting one side of the clamping means 1 has its base end (proximal end) fixedly attached to the inside of the distal end portion of the catheter 30 which is positioned inside the guiding catheter 31, and its distal end portion protruding from the distal end of the catheter 30 so that the needle part 2 can puncture a desired tissue when the catheter 30 protrudes from the guiding catheter 31.

Figure 8:
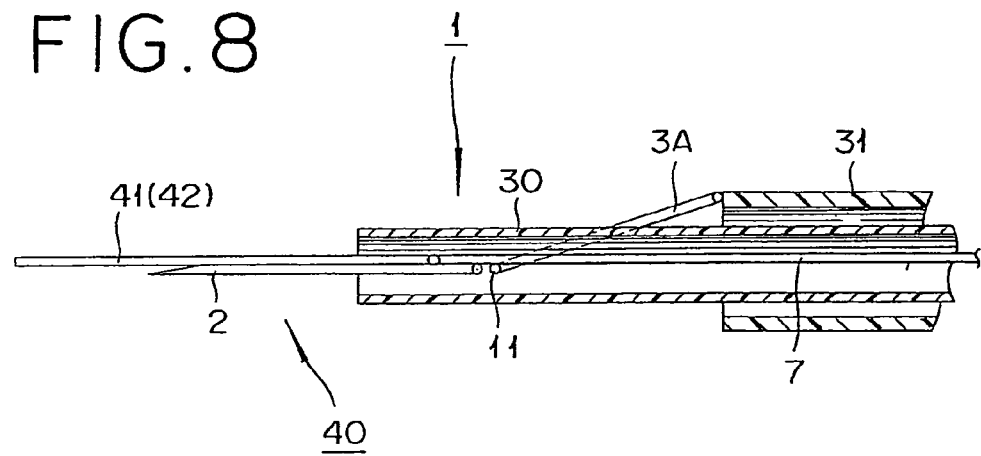
FIG. 8 is a schematic cross-sectional view showing the condition where a gripping member is in contact with a guiding catheter.

As shown in FIG. 6, the clamping member 3A constituting the other side of the clamping means 1 is composed only of a generally U-shaped wire member, having proximal ends (base ends) that are slightly bent. The bent proximal ends 11 are fitted into through-holes 12 opening into the catheter 30. The clamping member 3A is thus attached to the catheter 30 so as to be turnable relative to the catheter 30. Accordingly, at the time of storage in which the catheter 30 is axially retracted relative to the guiding catheter 31, the clamping member 3A is in a rearwardly fallen position (hereinafter referred to as rearward inclined position) as shown in FIG. 7. On the other hand, at the time of protrusion (in the condition where the catheter 30 protrudes forwardly relative to the guiding catheter 31, the external restrictive force exerted by the guiding catheter 31 is released, the clamping member 3A rises due to its own elasticity as shown in FIG. 8, and is pushed by a distal end portion of the guiding catheter 31, to be turned as indicated by the arrow in FIG. 9. Thus, the clamping member 3A is shifted from the dot-dash-line state to the solid-line state in FIG. 9 so that the clamping member 3A is positioned in a forwardly protruded position (hereinafter referred to as the forward protruded position).

The clamping member 3A composed only of the-U-shaped wire member need not necessarily be elastic. The clamping member 3A preferably has an outside diameter of 0.1 to 2 mm. As the material forming the clamping member 3A, SUS is ordinarily used. However, other materials which do not exert a bad effect on living bodies can also be used, for example gold, silver, platinum, tungsten, palladium, titanium, or alloys thereof.

The positioning means 40 includes a pair of comparatively long elastic wire members 41, 42, and a cable-like operating member 7 connected to a bundled proximal end (base end) portion of the elastic wire members 41, 42, and is so provided that it can be moved forwards and rearwards in the catheter 30. The cable-like operating member 7 may be slidably positioned in a long tube, for achieving smoother operations. The pair of elastic wire members 41, 42 have distal ends that protrude distally relative to the distal ends of the pointed members forming the needle part 2 and that open wide to form a contained angle of about 90 degrees when their proximal end portions are located at the proximal (base) portion of the needle part 2.

At the time of storage, the elastic wire members 41, 42 are contracted towards one another or restrained by the guiding catheter 31. However, when the catheter 30 is moved to protrude from the guiding catheter 31, the restraint is removed, and the elastic wire members 41, 42 open wide (spread out or diverge). Therefore, when the elastic wire members 41, 42 protrude from the catheter 30 in the condition where the catheter 30 protrudes from the right atrium R of the heart to the left atrium L of the heart, the elastic wire members 41, 42 make springy (elastic) contact with the aperture edge of the PFO 0, and display a self-centering function due to the exhibited elasticity.

Preferred specific examples of the elastic wire members 41, 42 are metal wires of stainless steel, nickel-titanium alloy, superelastic alloy (e.g., Ni—Ti alloy), or the like, with outside diameter of about 0.1 to 0.5 mm. Incidentally, the elastic wire members 41, 42 comprising the positioning means 40 are not limited to a pair of wire members, and may be provided in a greater number.

The sue and operation of this second embodiment of the PFO closing device is now described.

First, the operator operates the operating member 7 so that the needle part 2 and the clamping member 3A are stored inside the catheter 30 as shown in FIG. 7. After the same operation as in the first embodiment has been conducted and the distal end of the guiding catheter 31 has reached the position of the PFO 0, the catheter 30 is inserted into the guiding catheter 31.

When the distal end of the catheter 30 is positioned so that it protrudes from the right atrium R of the heart through the PFO 0 to the left atrium L of the heart, the operating member 7 is operated to move the elastic wires 41, 42 such that they protrude from (distally beyond) the distal end of the catheter 30. This ensures that the elastic wire members 41, 42 are released from the restraint due to the guiding catheter 31, and open wide to the opened condition. When the elastic wire members 41, 42 are slightly moved rearwards (proximally) by the operating member 7 starting from the opened condition, the elastic wire members 41, 42 make springy (elastic) contact with the aperture edge of the PFO 0. As a result, the elastic wire members 41, 42 display a self-centering function due to their elasticity, whereby the needle part 2 is located at the center of the PFO 0.

Figure 9:
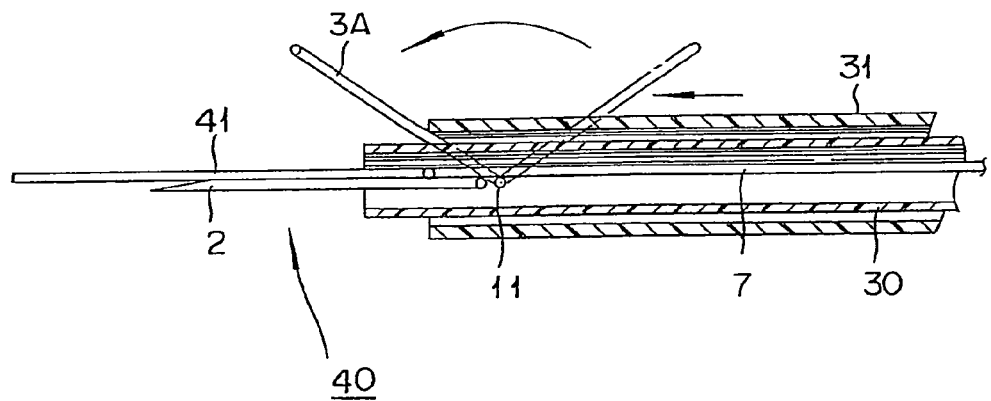
FIG. 9 is a schematic cross-sectional view showing the condition where the gripping member is pushed by the guiding catheter.

When the whole part of the catheter 30 together with the guiding catheter 31 in this condition is pushed forwards (distally), the pointed members of the needle part 2 puncture the SP M2 in the vicinity of the PFO 0. Also, when the catheter 30 is pushed forwards (distally) relative to the guiding catheter 31, the clamping member 3A rises (pivots forwards) from the rear inclined position, as shown in FIG. 8. When the guiding catheter 31 is slightly moved forwards starting from this condition, the clamping member 3A is pushed by a distal end portion of the guiding catheter 31, to be turned into the forward protruded position, as shown in FIG. 9.

When the guiding catheter 31 is pushed further forwards, the clamping member 3A is pushed by the guiding catheter 31, and is displaced toward the side of the needle part 2, so that the SS M1 and the SP M2 are clamped between the clamping member 3A and the needle part 2.

While maintaining this clamping condition, the electricity supplying unit is operated or controlled to supply a predetermined current through the lead wires 21, 22 in the same manner as in the first embodiment, whereon a current is passed between the clamping member 3A and the needle part 2, and the tissues of the SS M1 and the SP M2 are fused to each other.

After both the tissues are fused together, the passage of current is stopped, and the catheter 30 is retracted into the guiding catheter 31, whereby the positioning means 40 and the clamping member 3A are stored, followed by evulsion of the guiding catheter 31 together with the catheter 30.

A third embodiment of the PFO closing device is shown in FIGS. 10-19. In the description which follows, features of the third embodiment of the closing device which are the same as those associated with the embodiments described above are identified by the same reference numeral, and a detailed description of such features is not repeated.

In this embodiment, a support 50 is provided at the distal end (tip) of a catheter 30. In this illustrated embodiment, the support 50 is in the form of a multi-lumen type support 50. The needle part 2, the clamping member 3B and the positioning means 40 pass respectively through the lumens in the support 50 to help facilitate compact and smooth operations.

Figure 10:
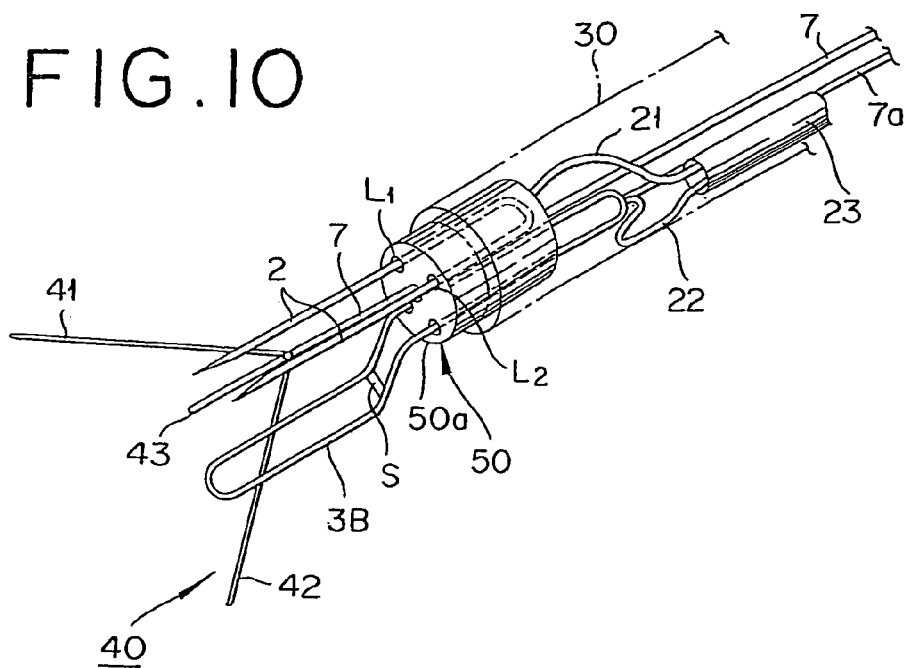
FIG. 10 is a schematic perspective view of a third embodiment of the PFO closing device disclosed herein.
Figure 11:
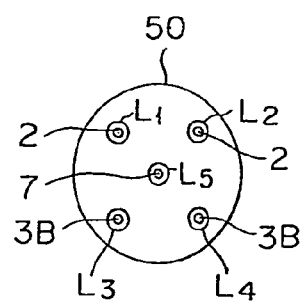
FIG. 11 is a front view of a support.

As shown in FIG. 10, the support 50 is positionally fixed at the distal end portion inside the catheter 30. As shown in FIG. 11, the support 50 has five lumens. The elongated members of the needle part 2 pass through first and second lumens L1, L2 in the support 50, and are positionally fixedly attached to the support 50. The spaced apart legs of the clamping means 3B pass through third and fourth lumens L3, L4 in the support 50, and an elongated cable-like operating member 7 of the positioning means 40 passes through a fifth lumen L5 at the center of the support 50. The support 50 may not necessarily be provided separately from the catheter 30. Instead, a catheter 30 provided therein with a plurality of lumens (multilumen catheter) may also be used.

Energy supplying means similar to that shown in FIG. 1 includes one lead wire 21 connected to the proximal end of the needle part 2 and another lead wire 22 connected to an operating member 7a for protruding (forwardly moving) and retracting (rearwardly moving) the clamping member 3B through the support 50, and the lead wires 21, 22 are connected to the electricity supplying unit in a manner similar to that described above.

Figure 12:
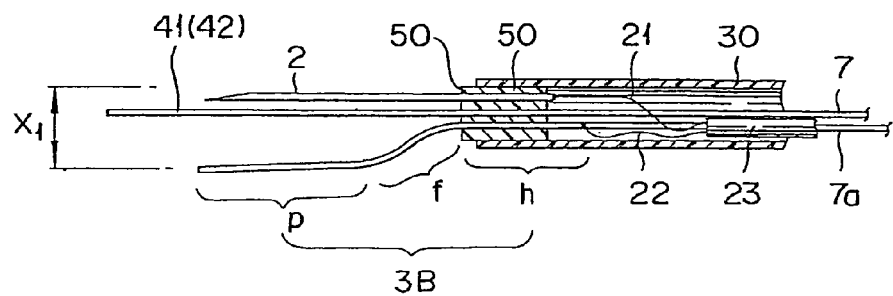
FIG. 12 is a side cross-sectional view of the third embodiment of the closing device.

More specifically, as shown in FIG. 10, the clamping member 3B in this embodiment is composed of a single elastic wire member having an arc-shaped distal end portion so that the overall shape is hairpin-like in shape (with spaced apart legs connected by a curved distal end portion). In side view, as shown in FIG. 12, the clamping member 3B has a horizontal part h located inside the support 50, a bent part f at the distal end (tip) of the horizontal part 2a, and a distal end (tip) part p extending from the bent part f in a tapering manner so as to gradually move away from the needle part 2, so that the distance between the distal end of the distal end part p and the needle part 2 is considerably large (increases in the distal direction) as indicated by $X_1$.

Figure 14:
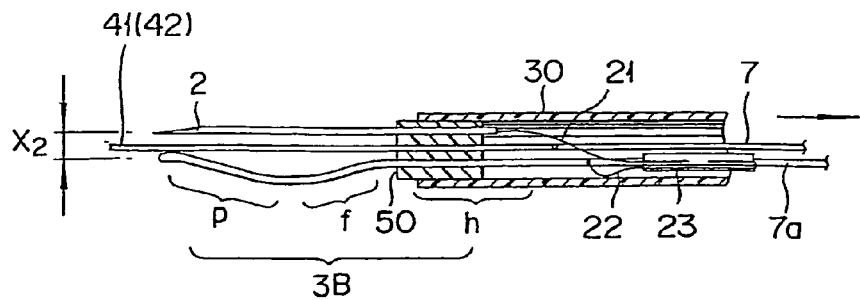
FIG. 14 is a side cross-sectional view of a part of the third embodiment of the device showing the gripping condition.

Therefore, when the operating member 7a connected to the rear (proximal) side of the clamping member 3B is pulled, the wire member constituting the clamping member 3B receives a drag from the end portions of the lumens in the support 50, i.e., from the catheter side to be thereby deformed as a whole toward the needle part 2, as shown in FIG. 14. The distance between the distal end of the distal end part p and the needle part 2 is considerably reduced, as indicated by $X_2$ in FIG. 14.

Figure 13:
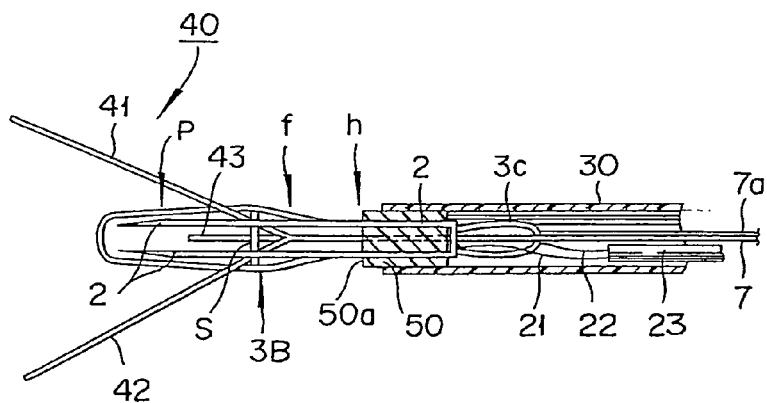
FIG. 13 is a plan cross-sectional view of the third embodiment of the closing device.

In plan view, as shown in FIG. 13, the clamping member 3B is so set as to have a width comparable to that of the needle parts 3. In addition, as shown in FIG. 10, in the vicinity of the bent part f, there is provided a bridge-like stopper part S which abuts against the front face 50a of the support 50, thereby preventing the clamping member 3B from retracting more than necessary (limiting the amount of retraction or rearward movement of the clamping member 3B relative to the support 50) during retraction of the clamping member 3B into the support 50.

Positioning means 40 includes a pair of elastic wire members 41, 42 similar to those in the second embodiment. In addition, a positioning wire 43 shown in FIG. 13 which is adapted to abut on the PFO 0, is provided at a central position between the pair of elastic wire members 41, 42. The operating member 7 is connected to a proximal end (base end) part formed by bundling the wire members so that the positioning means 40 as a whole can be moved forwards and rearwards (distally and proximally) along the lumens in the support 50 by operating the operating member 7.

The material forming the clamping member 3B, is preferably a SUS material with an outside diameter of 0.1 to 2 mm. However, other materials which do not exert bad influences on the living bodies may also be used, for example gold, silver, platinum, tungsten, palladium, or alloys thereof, Ni—Ti alloy, titanium alloys, etc. With respect to the operating member 7 and the positioning means 40, wire members formed of such material as SUS, gold, silver, platinum, tungsten, palladium, alloys thereof, Ni—Ti alloy, titanium alloys, etc. and having an outside diameter of 0.1 to 0.5 mm can be used.

The operation and use of this embodiment is now described.

FIGS. 15-19 show a procedure involving operating the PFO closing device according to this embodiment.

First, the operator positions the parts of the closing device so that the needle part 2 and the clamping member 3B are stored or positioned in the guiding catheter 31. Then, the guiding catheter 31 is inserted through the inferior vena cava J into the patient's body.

Figure 15:
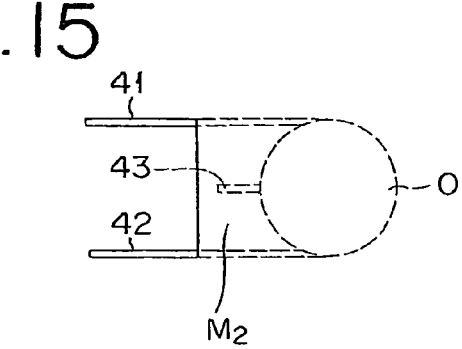
FIG. 15 is a view showing the inserted condition of positioning means.

When a distal end portion of the guiding catheter 31 has reached the vicinity of the PFO 0, an inserting operation is performed so that the distal end of the catheter 30 passes from the right atrium R of the heart through the PFO 0 to protrude into the left atrium L of the heart (see FIGS. 1, 4, and 5). When the distal end of the catheter 30 has protruded into the left atrium L of the heart, the operating member 7 is operated so that the pair of elastic wire members 41, 42 protrude from or beyond the distal end of the catheter 30, and the catheter 30 and the clamping member 3B are retracted. This helps ensure that the elastic wire members 41, 42 are opened wide, and then the operating member 7a is operated so as to slightly return (move back) the elastic wire members 41, 42, whereby the elastic wire members 41, 42 are brought into springy contact with the aperture edge of the PFO 0, as shown in FIG. 15 as viewed from the side of the left atrium L of the heart. As a result, the self-centering function is displayed in the same manner as in the above embodiments, whereby the needle part 2 is located at the center of the PFO 0. In addition, a proximal end portion of the positioning wire 43 abuts on an edge portion of the PFO 0 constituting an end portion of the SS M1, whereby the position of puncture by the needle part 2 is better secured.

Figure 16A:
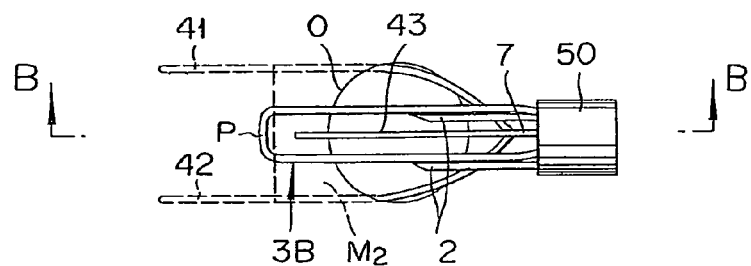
FIG. 16A is a front view of a PFO part as viewed from the side of a right atrium of heart R.
Figure 16B:
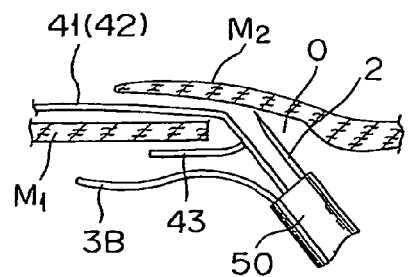
FIG. 16B is a cross-sectional view along the section line B-B of FIG. 16A.

FIG. 16A is a front view of the PFO portion as viewed from the side of the right atrium R of the heart, and FIG. 16B is a sectional view along the line B-B of FIG. 16A. In the condition where the elastic wire members 41, 42 are opened wide, as shown in FIG. 16A, the distal end part p of the clamping member 3B is located in the vicinity to be pressed of the SP M2, and the needle part 2 is located nearly at the center of the PFO 0. The positioning wire 43 abuts on an end portion of the SS M1, as shown in FIG. 16B, whereby the position of gripping at the entrance portion of the PFO 0 by the needle part 2 and the clamping member 3B is determined accurately. In addition, the positioning wire 43 also displays the function of pressing the SS M1 from the back side.

Figure 17:
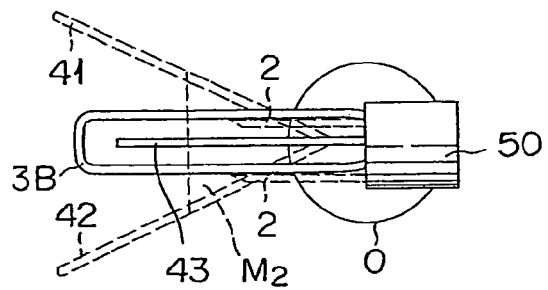
FIG. 17 is a view showing a puncture condition.
Figure 18:
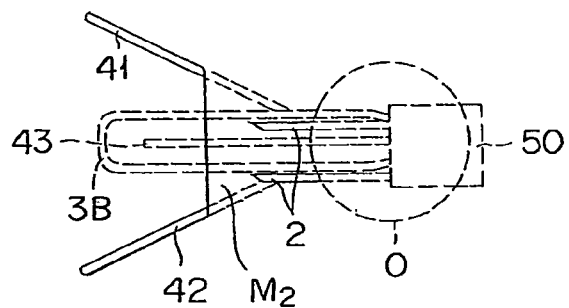
FIG. 18 is a view showing the puncture condition as viewed from the side of the left atrium of heart.

FIG. 17 is a view of the puncturing condition from the side of the right atrium R of the heart, and FIG. 18 is a view of the puncturing condition from the side of the left atrium I of the heart. In this condition, when the whole part of the catheter 30 is pushed forwards (distally) together with the guiding catheter 31, the needle part 2 punctures the SP M2 in the vicinity of the PFO 0 as shown in FIG. 18, and the clamping member 3B is also moved together with the needle part 2, to a forwardly moved position, as shown in FIG. 17. The SP M2 is deformed into a sector shape due to the wide opening of the aperture edge of the PFO 0 by the elastic wire members 41, 42. At this stage, there is a spacing of about XI between the clamping member 3B and the needle part 2, so that the SS M1 and the SP M2 are simply located between the needle part 2 and the clamping member 3B.

Figure 19:
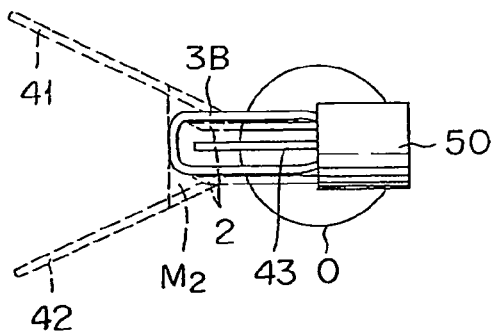
FIG. 19 is a view of a clamping condition as viewed from the side of the right atrium of heart.

FIG. 19 is a view of the puncturing condition from the side of the right atrium R of the heart. In this condition, when the operating member 7a of the clamping member 3B is pulled axially rearwards, the clamping member 3B is retracted along the lumens in the support 50, the bent part f of the operating member 7a is deformed by the end portions of the lumens in the support 50 toward the side of the needle part 2, thereby firmly clamping the SS M1 and the SP M2 between itself and the needle parts 2. While maintaining this clamping condition, the electricity supplying unit is operated or controlled to supply a predetermined current through the lead wires upon which the current is passed between the clamping member 3B and the needle part 2, whereby the tissues of the SS M1 and the SP M2 are fused to each other.

When the tissues are thus fused together, the passing of current is stopped, the operating member 7 is pulled to retract the positioning means 40, the operating member 7a is operated to separate the clamping member 3B from the tissue, these members are retracted into the inside of the guiding catheter 31 to attain the storage condition, and the guiding catheter 31 is evulsed. While the tissues are gripped by moving the clamping member 3B by operating the operating member 7 in this embodiment, a method of clamping the tissues through a sliding operation of the guiding catheter 31 may also be adopted as in the above-described embodiment. Also, the gripping of the tissues by the clamping member 3B may be conducted after evulsing the positioning means 40 following the puncture.

A fourth embodiment of the PFO closing device is shown in FIGS. 20-24. In the description which follows, features of this embodiment of the closing device which are the same as those associated with the embodiments described above are identified by the same reference numerals, and a detailed description of such features is not repeated.

Figure 20:
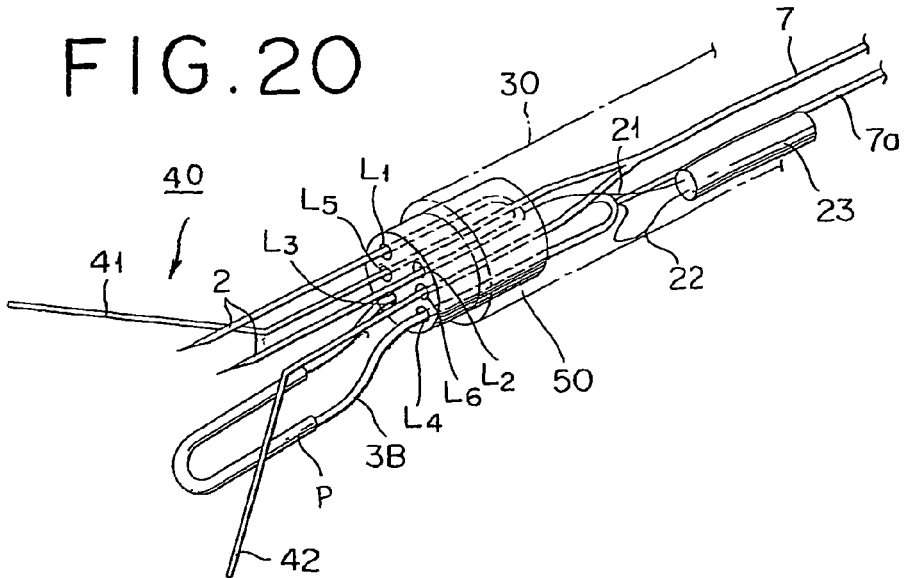
FIG. 20 is a schematic perspective view of a fourth embodiment of the PFO closing device disclosed herein.
Figure 21:
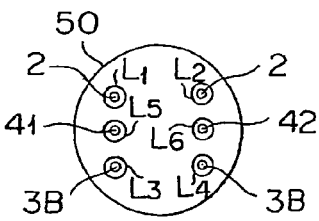
FIG. 21 is a front view of a support.
Figure 22:
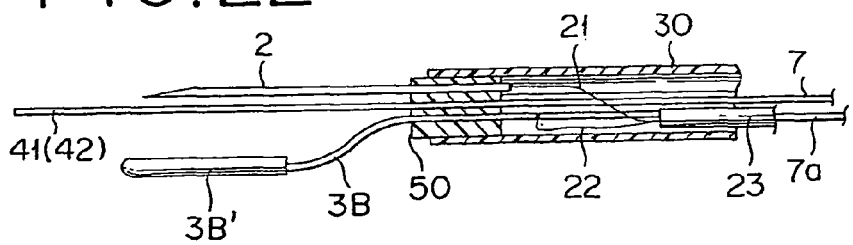
FIG. 22 is a side view of the fourth embodiment of the device shown in FIG. 21.
Figure 23:
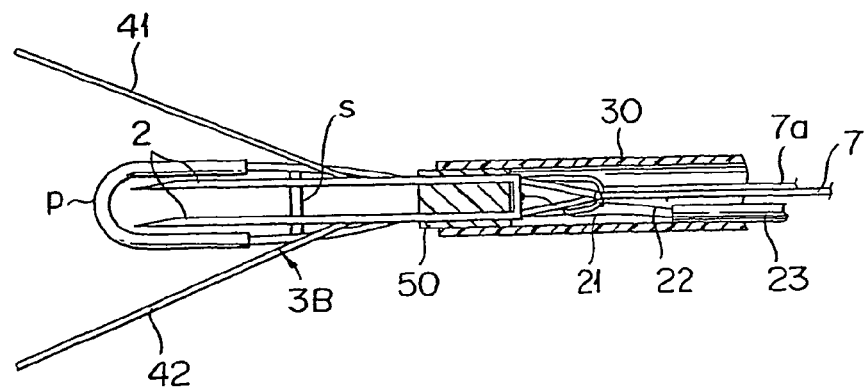
FIG. 23 is a plan cross-sectional view of the fourth embodiment of the device.
Figure 24:
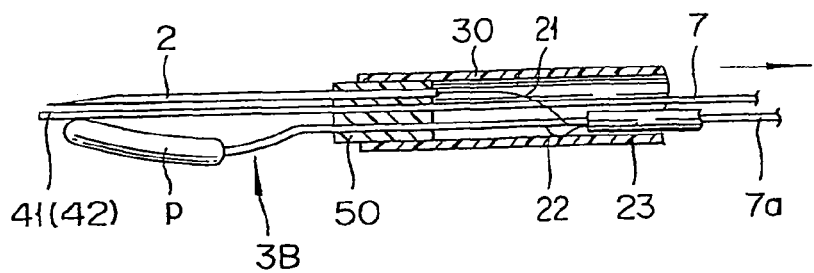
FIG. 24 is a side cross-sectional view of a part of the device showing the gripping condition of the fourth embodiment.

This fourth embodiment is basically the same as the third embodiment, except that the positioning means 40 and the gripping member (clamping member) 3B are somewhat different. As shown in FIGS. 20 and 21, a support 50 is provided with six lumens. The elongated members of the needle part 2 pass through first and second lumens L1, L2 of the support and are positionally fixedly attached to the support 50. The spaced apart legs of the clamping member 3B pass through the third and fourth lumens L3, L4 of the support 50, and the positioning means 40 passes through fifth and sixth lumens L5, L6 located at intermediate positions between the lumens L1, L2 and L3, L4.

The positioning means 40 in this embodiment is composed of a pair of elastic wire members 41, 42. The elastic wire members 41, 42 are independently inserted respectively in the fifth lumen L5 and the sixth lumen L6, and are so bent as to diverge away from each other at the distal end (tip) side, thereby being opening wider. On the other hand, the wire members 41, 42 are bundled on the proximal (rear) end side, and connected to an operating member 7. Therefore, when the operating member 7 is operated, the elastic wire members 41, 42 are moved together forwards or rearwards along the lumens in the support 50, and are opened wider or contracted, narrower under the restraint by the lumens L5, L6.

This construction helps ensure that the elastic wire members 41, 42 are supported by the lumens L5, L6. Therefore, even when a single operating member 7a is operated, the elastic wire members 41, 42 would not be rotated or deviated in the rotating direction but, instead, retain securely their positions of abutment on the PFO 0, whereby a centering function for the needle part 2 is displayed assuredly. In addition, the gripping member (clamping member) 3B in this embodiment is increased in diameter at a distal end part p thereof. By appropriately changing the outer diameter of the wire member itself constituting the gripping member (clamping member) 3B, it is possible to display the same stopper effect as that of the above-mentioned bridge-like stopper part S and an effect of enhancing the gripping force. The distal end part p can be increased in diameter not only by locally changing the outer diameter so as to obtain a step but also by covering the wire member constituting the gripping member (clamping member) 3B with another member so as to obtain a tongue-like member. This makes it possible to press the SP M2 against the pair of needle parts 2 in a wider area, thereby enhancing the fusing property. The other member is preferably formed of the same material as the material of the gripping member (clamping member) 3B.

The use and operation of this embodiment of the closing device will be described below. Since the operations of this embodiment are basically the same as those of the third embodiment, the following description will primarily discuss the positioning means 40. When the distal end of the catheter 30 inserted along the guiding catheter 31 has passed from the right atrium R of the heart through the PFO 0 to protrude into the left atrium L of the heart L, an operation of moving the single operating member 7 forwards (distally) is conducted. This helps ensure that the elastic wire members 41, 42 protrude from the distal end of the catheter 30, and the elastic wire members 41, 42 are spaced away from each other to come into the wide-opened state.

When the elastic wire members 41, 42 are slightly moved rearwards (proximally) by operating the operating member 7 starting from the wide-opened condition, the elastic wire members 41, 42 come into springy contact with the aperture edge of the PFO 0, to display the self-centering function in the same manner as in the above embodiments, whereby the needle part 2 is located at the center of the PFO 0.

When the procedure is completed, the operating member 7 is pulled to retract the elastic wire members 41, 42 along the lumens in the support 50. After the elastic wire members 41, 42 are retracted into the inside of the guiding catheter 31 to obtain the storage condition, the guiding catheter 31 is evulsed. The gripping of the tissues by the clamping member 3B may be conducted after the positioning means 40 is evulsed after puncture, in the same manner as in the third embodiment. While the clamping member 3B is fixed by operating the operating member 7 in this embodiment, a method of gripping the tissues through a sliding operation of the guiding catheter 31 may be adopted, in the same manner as in the above embodiments.

Figure 25:
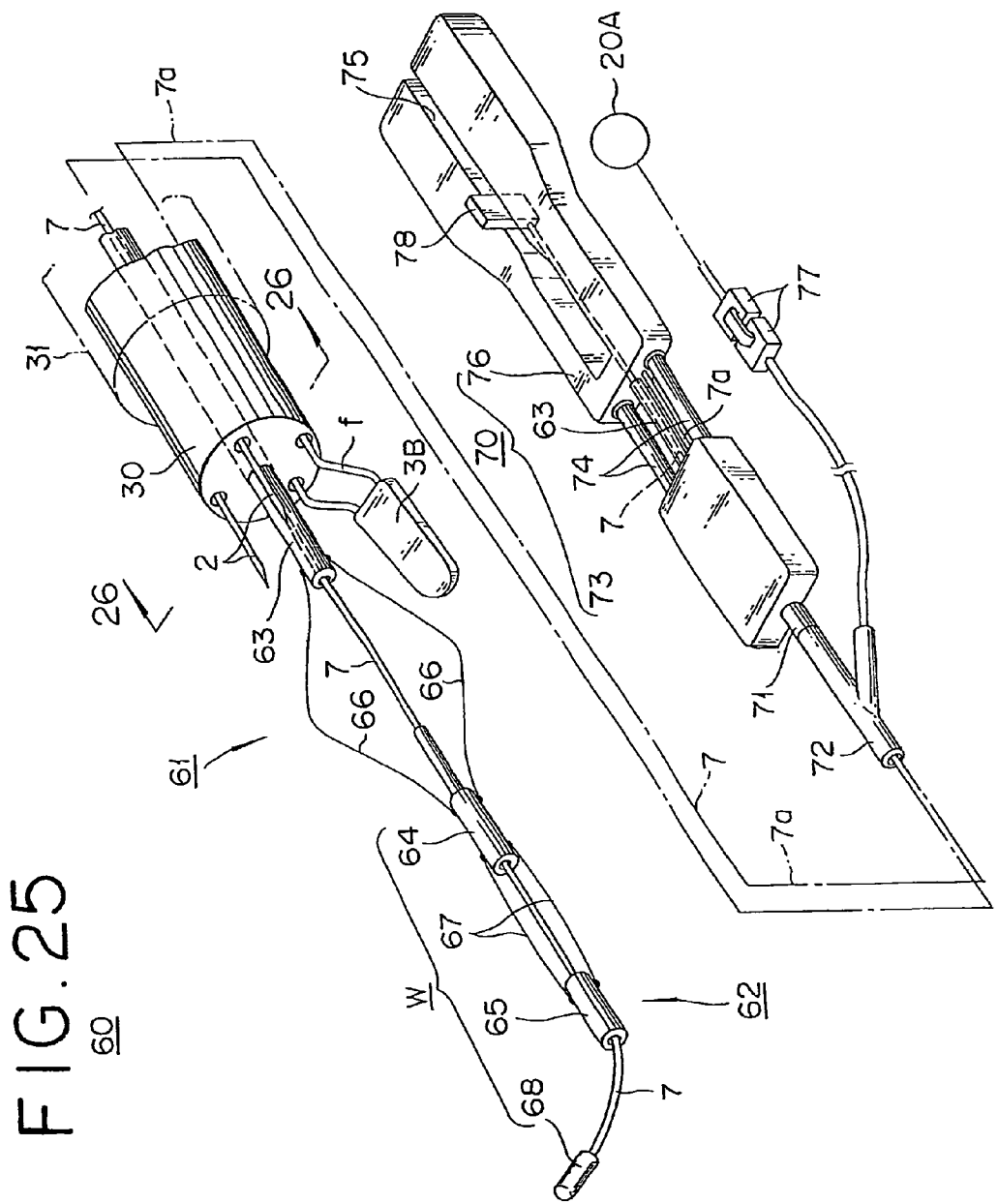
FIG. 25 is a schematic perspective view of a PFO closing device according to a fifth embodiment disclosed herein.
Figure 26:
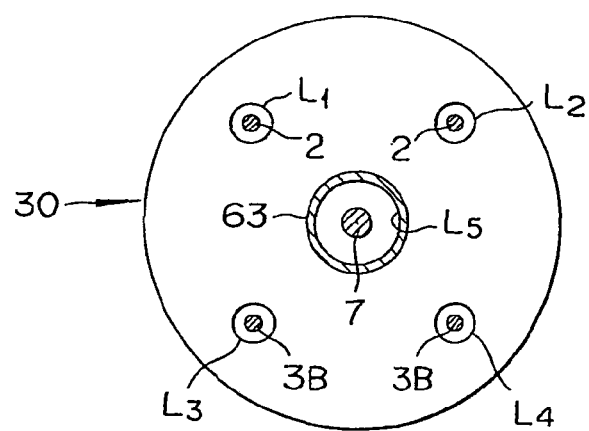
FIG. 26 is an end cross-sectional view taken along the section line 26-26 of FIG. 25.
Figure 27:
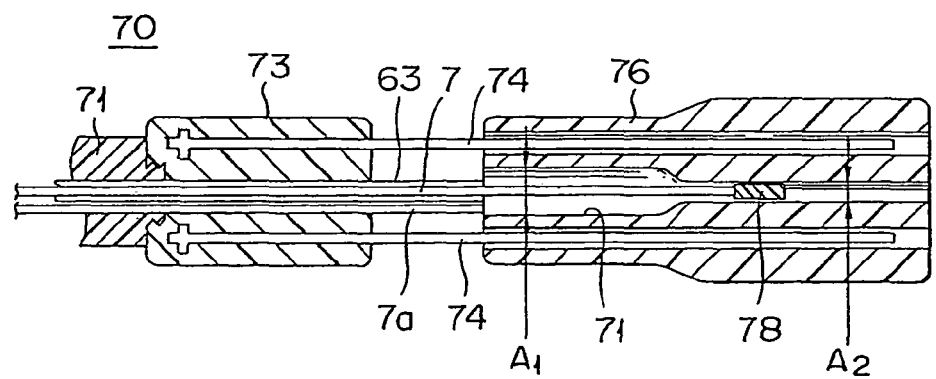
FIG. 27 is a cross-sectional plan view of a hand-operated operating part of the PFO closing device.

FIGS. 25-27 illustrate a fifth embodiment of the PFO closing device. In the description which follows, features of this embodiment of the closing device which are the same as those associated with the embodiments described above are identified by the same reference numeral, and a detailed description of such features is not repeated.

In the above-described embodiments, there is no holding means for securely holding the SP M2 in a non retractable manner at the time of puncturing with the needle part 2. On the other hand, adopting a mechanism by which the holding means and the positioning means can be operated by a series of operations (hereinafter referred to as positioning and holding means) can facilitate the puncturing with the needle part 2. In addition, the speediness and assuredness of the procedure are greatly enhanced, which naturally is preferable. Particularly, since the SP M2 is a membrane with a relatively small thickness of about 1 to 2 mm, it is liable to be broken or damaged. In view of this, when the SP M2 is held from the back side at the time of puncture, the procedure can be conducted relatively safely, without placing an irrational burden on the SP M2. This is highly preferable.

The configuration of this embodiment of the closing device is similar to those of the above-described embodiments regarding the aspects of the device other than the positioning and holding means.

As shown in FIG. 25, the positioning and holding means 60 in this embodiment generally comprises a positioning part 61 for positioning the needle part 2 in relation to the PFO 0, and a holding part 62 for holding the SP M2 non-retractably in relation to the puncturing direction of the needle part 2. The positioning and holding means 60 is configured so that when a long or elongated operating member 7 movably positioned in a catheter 30 to be movable forwards (distally) and rearwards (proximally) protrudes from the distal end of the catheter 30 and is moved axially forwards or rearwards, the positioning part 61 and the holding part 62 can thereby be operated continuously.

The positioning and holding means 60 is provided at a distal end portion of the catheter 30 which is outfitted with a plurality of lumens L (L is the generic symbol for lumens L1-L5 shown in FIG. 26) extending along the axial direction, and is normally stored in a guiding catheter 31. At the time of use, the positioning and holding means 60 is pushed out from the guiding catheter 31.

The catheter 30 in this embodiment is one in which the lumens are a part of the catheter 30 rather than a support, and the configuration is such that the catheter 30 can be thought of as being obtained by elongating the above-mentioned support 50. The catheter 30 is provided therein with five lumens. The operating member 7 is movably positioned in an elastic main tube 63 in a manner permitting forward and rearward movement of the operating member 7. The elastic main tube 63 and the operating member 7 pass through a centrally located lumen L5 so that the positioning part 61 and the holding part 62 are operated by a hand-operated operating part 70 connected to the proximal end side of the operating member 7. In the following description, the hand-operated operating part side of the PFO closing device is referred to as "the proximal side", and the side of the needle part 2 or the SP M2 is referred to as "the distal side".

The positioning and holding means 60 includes the positioning part 61 and the holding part 62. The positioning part 61 includes the main tube 63, the operating member 7, and a pair of first elastic wire members 66. The main tube 63 is positioned in the central lumen L5 having the maximum aperture diameter of the five lumens L1-L5, for reinforcing the catheter 30 and recovering (by pulling) the positioning and holding means 60 into the catheter 30. The operating member 7 is axially movable forwards and rearwards in the main tube 63. The two first elastic wire members 66, which are movable away from each other to open wider and towards one another to contract narrower by the operation of the operating member 7, connect the main tube 63 and an intermediate sleeve body 64 to each other. The holding part 62 includes an enlarged distal end portion 68 of the operating member 7, a tip sleeve body 65 spaced in the proximal direction from the contact member 68, and a pair of second elastic wire members 67 connecting the intermediate sleeve body 64 and the tip sleeve body 65 to each other. In the illustrated embodiment, the enlarged distal end portion of the operating member 7 is constituted by a contact member 68 provided at the distal end portion of the operating member 7. The contact member 68 and the tip sleeve body 65 are adapted to hold the SP M2.

The positioning part 61 centers the needle part 2 relative to the PFO 0 by protruding the operating member 7 from the distal end of the main tube 63 and operating the operating member 7 to move axially forwards, thereby displacing the first elastic members 66 outwards so that the first elastic members 66 press the inner edge of the PFO 0 with springy (elastic or biasing) forces which are substantially equal. In short, the positioning part 61 functions to position the needle part 2 located between the first elastic members 66 at a central portion of the PFO 0.

The holding part 62 has a curving mechanism W for curving the distal end portion of the operating member 7 through operation of the operating member 7 to move axially forwards or rearwards. The curving mechanism W functions to curve the holding part 62 oppositely to the direction of puncturing the SP M2 with the needle part 2, so as thereby to hold the SP M2. The curving mechanism W includes the intermediate sleeve body 64, the tip sleeve body 65, the second elastic wire members 67 connecting the sleeve bodies 64, 65 to each other, and the contact member 68.

The proximal ends of the first elastic wire members 66 are secured or fixed (e.g., welded) to the distal end of the main tube 63, and the distal ends of the first elastic wire members 66 are fixed (e.g., welded) to the intermediate sleeve body 64. On the other hand, the proximal ends of the second elastic wire members 67 are secured (e.g., welded) to the distal end of the intermediate sleeve body 64, and the distal ends of the second elastic wire members 67 are fixed (e.g., welded) to the tip sleeve body 65.

Preferable specific examples of the first and second elastic wire members 66, 67 are metal wires formed of stainless steel, nickel-titanium alloy, superelastic alloy (e.g., Ni—Ti alloy) or the like, with an outer diameter of about 0.1 to 0.5 mm. In addition, the metal wire may be covered with a resin (flexible) tube, for preventing the elastic wire members 66, 67 from damaging the tissues.

The holding part 62 is configured so that the first elastic wire members 66 on the proximal side are curved prior to curving of the second elastic wire members 67 on the distal side, to position the needle part 2, and then the operating member 7 itself is deformed while being accompanied by the contact member 68 and the tip sleeve body 65, so as to hold the SP M2 after the needle part 2 is positioned by the positioning part 61.

Such a configuration is not particularly limited however. For example, there may be adopted an alternative in which the second elastic wire members 67 are formed of a material higher in stiffness than that for the first elastic wire members 66, or an alternative in which a part of the first elastic wire members 66 is preliminarily worked by bending or the like to form more easily deformable parts so that the first elastic wire members 66 are curved prior to curving of the second elastic wire members 67 through deformation of the easily deformable parts when a pulling force is exerted thereon. This helps ensure that, with only the operating member 7 pulled rearwards, the first elastic wire members 66 on the proximal side come into abutment on the inner edge of the PFO 0, thereby positioning the needle part 2. With the operating member 7 pulled further, the second elastic wire members 67 on the distal side are thereafter deformed in the manner of projecting in an arcuate shape radially outwards, whereby the SP M2 can be held non-retractably so that the puncture with the needle part 2 can be performed relatively easily.

As shown in FIGS. 25 and 26, the hand-operated operating part 70 generally includes a first operating body 73 and a second operating body 76. The proximal end of the catheter 30 is connected through a connecting member 71 and a Y connector 72 to the first operating body 73. The second operating body 76 is provided with through-holes permitting passage therethrough of a pair of slide rails 74 projecting from the proximal end of the first operating body 73. The second operating body 76 is able to move toward and away from the first operating body 73 by sliding along the slide rails 74. In FIG. 25, only the hand-operated operating part 70 is shown in reduced size for convenience of space.

The main tube 63 passes through the inside of the first operating body 73, and its proximal end is connected to the distal end of the second operating body 76. Therefore, with the second operating member 76 pulled rearwards, the whole part of the positioning and holding means 60 can be recovered into the central lumen L5 of the catheter 30. The main tube 63 may be formed of a deformable elastic material such as polyimide resin, polyurethane, PET, nylon, fluoro-resin, polypropylene, etc. In addition, the hand-operated operating part 70 may be formed by use of a metallic pipe and be connected to the main tube 63 formed of an elastic material.

The proximal end of the operating member 7 is attached to a grip 78 which is reciprocally slidable in a slide groove 75 formed in the center of the second operating body 76. By reciprocally sliding the grip 78 in the slide groove 75, the whole part of the operating member 7 is reciprocated in the main tube 63.

As shown in FIG. 27, the slide groove 75 is formed so that the width A1 of the front half portion thereof is greater than the width A2 of the rear half portion thereof. This helps ensure that, in the case where the grip 78 is located in the front half of the slide groove 75, the grip 78 can be inclined in a direction orthogonal to the axis of the slide groove 75, whereby the operating member 7 can be turned about its axis inside the catheter 30, so as to rotate and adjust the position of its distal end. As a result, when the operating member 7 is operated by operating the grip 78 in the hand-operated operating part 70, not only the position in the front-rear direction but also the rotational position can be adjusted. This enhances the procedure of inserting the device into the left atrium of the heart.

The needle part 2 constituting one side (one part) of the clamping means 1 may be formed in a U-shaped overall form and inserted in a lumen formed by breaking the portion of the catheter between the lumens L1 and L2. Alternatively, the individual elongated members of the needle part 2 may be disposed respectively in the lumens L1 and L2 as shown in FIG. 26. In any case, a lead wire is connected to the rear end(s) needle part(s) 2, and the lead wire passes through the Y connector 72 to the exterior, to be connected to the energy supplying means through a coupler 77.

The clamping member 3B constituting another part (other side) of the clamping means 1 has a distal end portion in which a generally U-shaped wire member is covered with a conductive material to provide a tongue-like member (plate member). The proximal ends of the wire members forming the clamping member 3B pass through the lumens L3 and L4 of the catheter 30, and are connected to a single operating member 7a. The operating member 7a is operative to move the clamping member 3B forwards and rearwards. In this embodiment, the operating member 7a is connected on the proximal side to a distal end portion of the second operating body 76.

The lead wires for the operating member 7a and the needle part 2 pass through the Y connector 72 to the exterior, and are connected to the electricity supplying unit 2OA through a predetermined switch.

The use and operation of this embodiment will now be described below with reference to FIGS. 28A-28D which are schematic views showing the operating conditions of the positioning and holding means. While the actual shapes and positions of the second elastic wire members 66 are substantially flush with those of the needle part 2 and the clamping member 3B, they are shown in the state of having been displaced by 90 degrees, for ease of understanding. Therefore, the deformed conditions shown in the figures are different from the actual deformed conditions.

First, the operator retracts (rearwardly moves) the second operating body 76 of the hand-operated operating part 70 in relation to the first operating body 73, to obtain the condition where the needle part 2 and the clamping member 3B are stored (positioned) in the guiding catheter 31. In this condition, using a guide wire as a guide by the ordinary method, the distal end of the guiding catheter 31 is inserted into the patient's body from a predetermined position of the body, to the right atrium R of the heart. It is to be understood that a method may be adopted in which only the guiding catheter 31 is inserted into the patient's, body, and thereafter the catheter 30 is inserted by use of the guiding catheter 31 as a guide. Next, by operating the first operating body 73, the distal end of the catheter 30 is passed from the right atrium R of the heart through the PFO 0 to protrude into the left atrium L of the heart. Thereafter, the grip 78 is moved forwards to thereby forwardly move the distal end of the operating member 7 so that it protrudes from the tip sleeve body 65 and is inserted into the left atrium L of the heart. This protruded condition can be visually confirmed externally if the contact member 68 or the like is provided with a marker. However, if the protrusion is accompanied by abutment of the distal end of the operating member 7 against the inside wall of the left atrium L of the heart or the like, the place where the distal end of the operating member 7 is located can be tactually confirmed, even where visual confirmation is difficult to achieve. This enhances the use and operation. Where the grip 78 is located in the wider front half portion of the slide groove 75 and is inclined, the tactual confirmation of the position of the distal end of the operating member 7 is facilitated.

After the position of the distal end of the operating member 7 is confirmed, the grip 78 is retracted until the contact member 68 of the operating member 7 abuts on the tip sleeve body

Figure 28A:
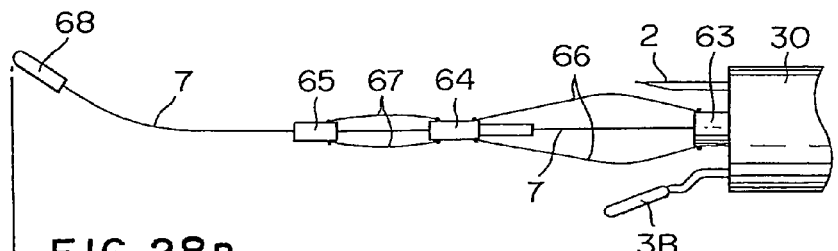
FIGS. 28A-28D are schematic views showing operating conditions of positioning and holding means in the fifth embodiment.
Figure 28B:
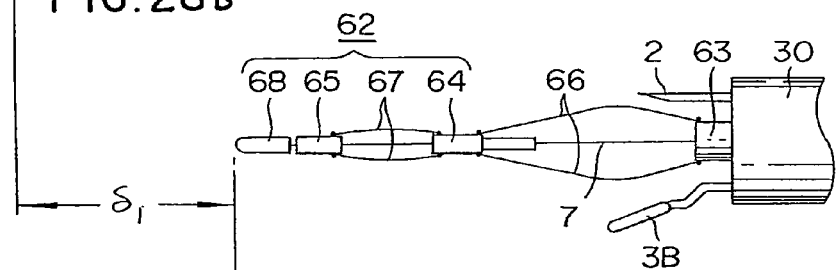

65, as shown in FIG. 28B (the retraction amount is "δ₁" in FIG. 28B). Then, the first operating body 73 is operated to locate the second elastic wire members 67, the needle part 2, and the clamping member 3B in the vicinity of the SP M2, and the whole body of the holding part 62 is inserted into the left atrium L of the heart.

Figure 28C:
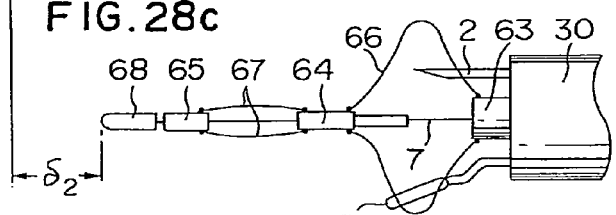

With the grip 78 retracted further (the retraction amount is "δ2" in FIG. 28C), the operating force of the retraction is transmitted by the operating member 7 and through the contact member 68, the tip sleeve body 65, the second elastic wire members 67, and the intermediate sleeve body 64 to the first elastic wire members 66 which are firmly attached to the distal end of the main tube 63. The first elastic wire members 66 are deformed so as to project in arcuate shapes radially outwardly, as shown in FIG. 28C. It should be noted here, however, the second elastic wire members 67 are not yet deformed in this instance.

As a result, the first elastic wire members 66 are deformed while pressing wider the aperture edge portion of the PFO 0, so that the needle part 2 proximate to the first elastic wire members 66 is centered relative to the PFO 0, i.e., the needle part 2 is located in the center of the PFO 0.

Figure 28D:
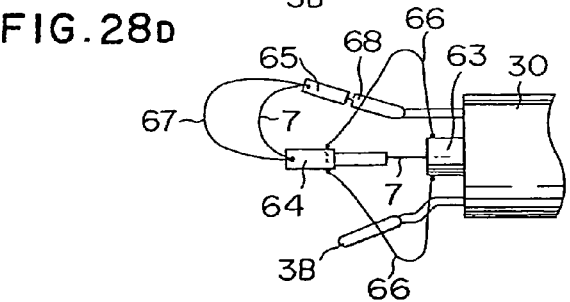

With the grip 78 retracted further until the proximal end of the intermediate sleeve body 64 abuts on the distal end of the main tube 63, as shown in FIG. 28D, the first elastic wire members 66 are not considerably more deformed, whereas the second elastic wire members 67 on the distal side curve and are deformed in the manner of projecting in arcuate shapes radially outwards as illustrated, under the above-mentioned operating force. As a result, inside the left heart atrium L, the contact member 68 and the tip sleeve body 65 come closer to the needle part 2, so that the contact member 68 and the tip sleeve body 65 abut on the face on the left atrium side of the SP M2, to hold the latter.

In this condition, the first operating body 73 is moved forwards, whereby the pointed elongated members of the needle part 2 provided at the distal end of the catheter 30 puncture the SP M2 at predetermined positions. The puncture condition is the condition shown in FIG. 1 in which the SS M1 and the SP M2 are present between the needle parts 2 and the clamping member 3B.

Once puncturing is accomplished, the position of the needle part 2 is fixed in relation to the SP M2. At this stage, therefore, the second operating body 75 is once returned to make the first elastic wire members 66 and the second elastic wire members 67 straight, as shown in FIG. 28B. Then, the second operating body 75 is retracted so that the whole body of the positioning and holding means 60 is recovered into the lumen L5 of the catheter 30 by the main tube 63.

At the time of this recovery, the operating member 7a of the clamping member 3B connected to the second operating body 75 also retracts the clamping member 3B along the lumens of the catheter 30, so that the bent part f of the clamping member 3B are deformed by an end portion of the catheter 30 toward the needle parts 2, to firmly clamp the SS M1 and the SP M2 between the clamping member 3B and the needle part 2.

While maintaining this clamping condition, the electricity supplying unit 2OA is operated or controlled to pass a predetermined current between the clamping member 3B and the needle part 2, whereby the tissues of the SS M1 and the SP M2 are fused to each other.

When the tissues are fused together, the passing of current is stopped, the first operating body 75 is retracted so that the needle part 2 and the clamping member 3B located at the distal end of the catheter 30 are stored into the guiding catheter 31 together with the positioning and holding means 60, and the guiding catheter 31 is evulsed from the patient's body.

FIG. 29 is a schematic perspective view of a sixth embodiment of the PFO closing device. While the positioning and holding means 60 in the fifth embodiment has had a configuration in which the first elastic wire members 66 in the positioning part 61 and the second elastic wire members 67 in the holding part 62 are composed of separate members, this embodiment adopts a configuration in which the two kinds of elastic wire members are integrated, to obtain a more simple configuration. The positioning and holding means 80 in this embodiment is configured such that the proximal end of a second sleeve body 81 is mounted to the main tube 63 protruding by a predetermined length from the distal end of the catheter 30, an operating member 7 provided in the main tube 63 protrudes from the distal end of the second sleeve body 81, and a contact member 68 is provided at the protruded distal end of the operating member 7.

A positioning part 61 is composed of a pair of positioning pieces 82 formed at a proximal (base) portion of the second sleeve body 81. In this case, the positioning pieces 82 are formed by slitting or cutting off a part of the second sleeve body 81, leaving end portions of the second sleeve body 81. The positioning pieces 82 are preferably formed in the shape of flat bands so that they make springy (elastic or biasing) contact with the inner edge of the PFO 0. The positioning pieces 82 are thus elastically deformable.

On the other hand, the holding part 62 has a configuration as follows. The second sleeve body 81 protruding from the main tube 63 is provided with two through-holes 83, 84 spaced in the axial direction. The operating member 7 leading from the main tube 63 into the second sleeve body 81 passes out to the exterior via the through-hole 84, is then returned into the second sleeve body 81 via the through-hole 83, and further extends and protrudes from the distal end of the second sleeve body 81. Thus, the operating member 7 extends through the second sleeve body 81 on the proximal side of the two through-holes 83, 84, extends outside the sleeve body 81 by way of the proximal most through hole 84, extends back into the sleeve body 81 by way of the distal most through hole 83, extends through the distal end portion of the sleeve body 81, and then exits the sleeve body through the open distal end of the sleeve body 81. A contact member 68 is provided at the protruding distal end of the operating member 7.

Here, the second sleeve body 81 may be any tube that is deformable. Preferably, however, the second sleeve body 81 is a tube which can be visually confirmed externally by use of X-rays or the like, and is preferably composed of a synthetic resin such as polyurethane, PET, nylon, polyethylene, polyimide, fluoro-resin, polypropylene, etc.

In use of the positioning and holding means 80 configured as above, when the operating member 7 is pulled by an operation, the contact member 68 abuts on the distal end of the second sleeve body 81, and the operating force in this instance acts on the entire second sleeve body 81 through the contact member 68. The positioning pieces 82 formed at a proximal (base) portion of the second sleeve body 81 are lower in stiffness than the other portions because of the formation of the slit or cutout. Therefore, the positioning pieces 82 are preferentially curved outwards, as if they were buckled, to abut on the inside surface of the PFO 0, thereby displaying a centering function, whereby the needle part 2 is positioned at predetermined positions.

With the operating member 7 pulled further, the second sleeve body 81 between the through-holes 83, 84 is curved, resulting in the SP M2 being held by the contact member 68 and the second sleeve body 81a on the distal side relative to the through-hole 83.

The positioning and holding means 80 in this embodiment thus has a configuration in which the second sleeve body 81 is mounted to the main tube 63 protruding from the catheter 30, and the second sleeve body 81 is provided with the positioning pieces 82 at a proximal (base) portion thereof and with the two through-holes 83, 84 in a distal end (tip) portion thereof. Therefore, the positioning and holding means 80 in this embodiment is simpler in configuration and advantageous in cost, as compared with that in the above-described embodiment.

The use and operations of the positioning and holding means 80 in this embodiment are substantially the same as in the fifth embodiment above. Therefore, the description of the use and operations is not repeated.

Figure 30:
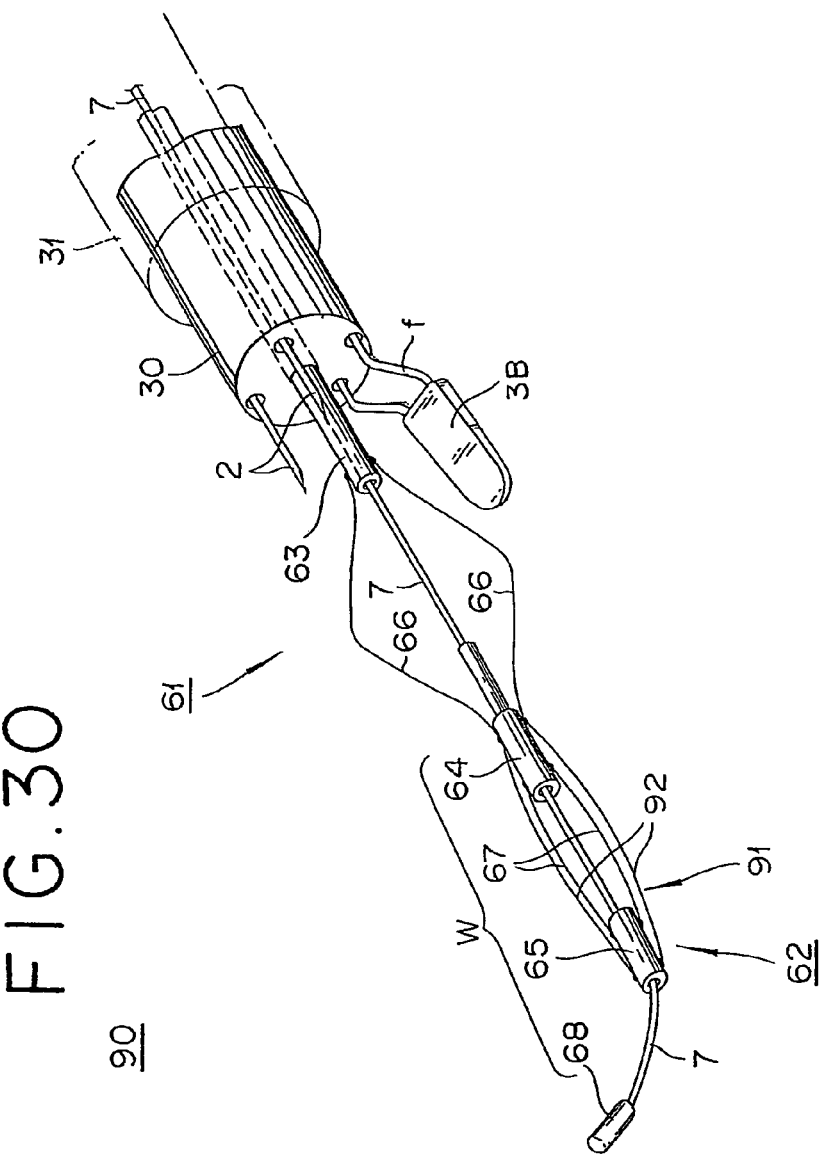
FIG. 30 is a schematic perspective view of a seventh embodiment of the PFO closing device.
Figure 31:
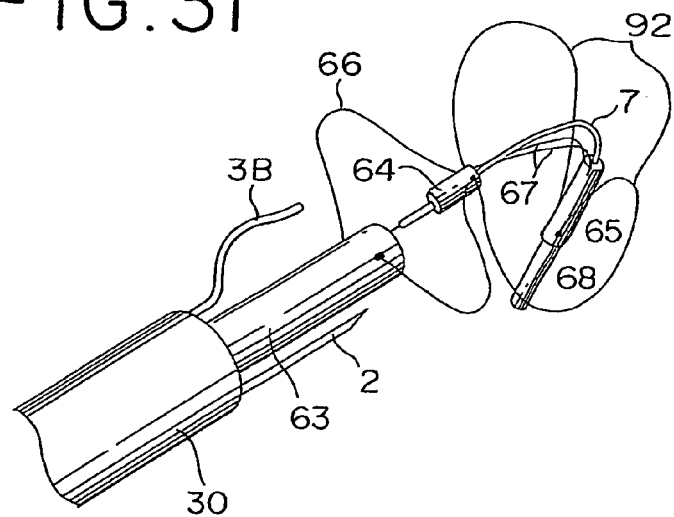
FIG. 31 is a schematic perspective view showing a deformed condition of the seventh embodiment.

FIGS. 30 and 31 illustrate a seventh embodiment of the PFO closing device. The positioning and holding means 90 according to this embodiment is similar in configuration to that in the fifth embodiment, except that it has a crease smoothing part 91 for smoothing out creases of the SP M2. The shapes of the PFO 0 and the SP M2 differ from person to person. Specifically, the SP M2 can possesses creases or be creased, which make it difficult to specify the position of puncture by the needle part 2. If the needle part 2 can be made to puncture the center of the SP M2 in the condition where the creases are smoothed out, the smoothness and facility of the procedure are enhanced, with the result that the assuredness of the treatment is enhanced, and the procedure can be carried out relatively safely and speedily, all of which is quite preferable.

In view of this, the positioning and holding means 90 in this embodiment generally has a positioning part 61 for positioning the needle part 2 in relation to the PFO 0, a holding part 62 for holding the SP M2 non-retractably in relation to the puncturing direction of the needle parts 2, and the crease smoothing part 91 for smoothing out the creases present in the SP M2. This embodiment is the same as the fifth embodiment above in that the positioning part 61 and the holding part 62 can be continuously operated by moving a long operating member 7 axially forwards and rearwards, but this embodiment is different from the fifth embodiment with respect to the inclusion of the crease smoothing part 91. Therefore, this aspect of the closing device will be described, and a detailed description of the other parts of the device, denoted by the same symbols as used above, is not repeated.

As shown in FIG. 30, the crease smoothing part 91 is composed of a pair of third elastic wire members 92 connecting the intermediate sleeve body 64 and the tip sleeve body 65 to each other. In the positioning and holding means 60 in the above-described embodiment, the intermediate sleeve body 64 and the tip sleeve body 65 are connected by only one pair of second elastic wire members 67. On the other hand, in the positioning and holding means 90 in this embodiment, the pair of third elastic wire members 92 are provided on the outside of the second elastic wire members 67.

The third elastic wire members 92, in the pre-deformation state shown in FIG. 30, are deformed so as to project radially outwards in substantially the same plane as the first elastic wire members 66. It is preferable that the third elastic wire members 92, in the post-deformation state as shown in FIG. 31, are opened radially outwards so largely as to smooth out the creases of the SP M2. In consideration of this point, in this embodiment, the third elastic wire members 92 are composed of members which are deformable in the manner of projecting outwards more easily than the first elastic wire members 66. To be more specific, the third elastic wire members 92 can be the same as the first elastic wire members 66 in outer diameter and material, but can be larger in length (longer) than the first elastic wire members 66. While the third elastic wire members 92 as shown in the figure are curved to some extent, they may be curved outwards to an even greater extent.

In the use of the positioning and holding means 90 configured as above, in the same manner as in the above-described embodiments, the distal end of a catheter 30 is passed from the right heart atrium R through the PFO 0 to protrude into the left heart atrium L, and the distal end of the operating member 7 is protruded from the tip sleeve body 65 and inserted into the left heart atrium L. Then, the operating member 7 is retracted until its contact member 68 abuts on the tip sleeve body 65, and the holding part 62 is inserted into the left heart atrium L.

With the operating member 7 retracted, the operating force is transmitted through the contact member 68, the tip sleeve body 65, the second elastic wire members 67, and the intermediate sleeve body 64 to the first elastic wire members 66 firmly attached to the distal end of a main tube 63, whereby the first elastic wire members 66 are deformed so that they project radially outwards into arcuate shapes. Where the projecting deformation of the first elastic wire members 66 is performed in the vicinity of the PFO 0, the needle part 2 can be centered in relation to the PFO 0. It should be noted here, however, that the second elastic wire members 67 and the third elastic wire members 92—are not yet deformed at this time.

By further retracting or rearwardly moving the operating member 7, as shown in FIG. 31, the second elastic wire members 67 on the distal side are curved. In addition, the third elastic wire members 92 are deformed in such a way that they project radially outwards into arcuate shapes. In this case, the third elastic wire members 92 are deformed in directions such as to smooth out the creases of the SP M2, i.e., in directions such as to projectingly deform along the plane of the SP M2, which is generally deviated by about 90 degrees from the plane in which the first elastic wire members 66 are deformed projectingly.

As a result, the contact member 68 and the tip sleeve body 65 hold the SP M2 from the left atrium L side of the heart, whereas the third elastic wire members 92 on the right atrium R side of the heart enter into the creases of the SP M2, to smooth out the creases.

Therefore, the operator can relatively assuredly puncture a predetermined position of the SP M2, held by the holding part 62 from the side of the left atrium L of the heart and with its creases smoothed out, by the needle part 2 located in the center of the PFO 0.

After the predetermined position or portion of the SP M2 is punctured with the needle part 2, the whole body of the positioning and holding means 90 is recovered into a lumen L5 of the catheter 30 by the main tube 63, whereon the SS M1 and the SP M2 are firmly clamped between a clamping member 3B and the needle part 2. While maintaining this clamped condition, an electric current is passed between the clamping member 3B and the needle part 2, whereby the tissues of the SS M1 and the SP M2 are fused together.

Figure 32:
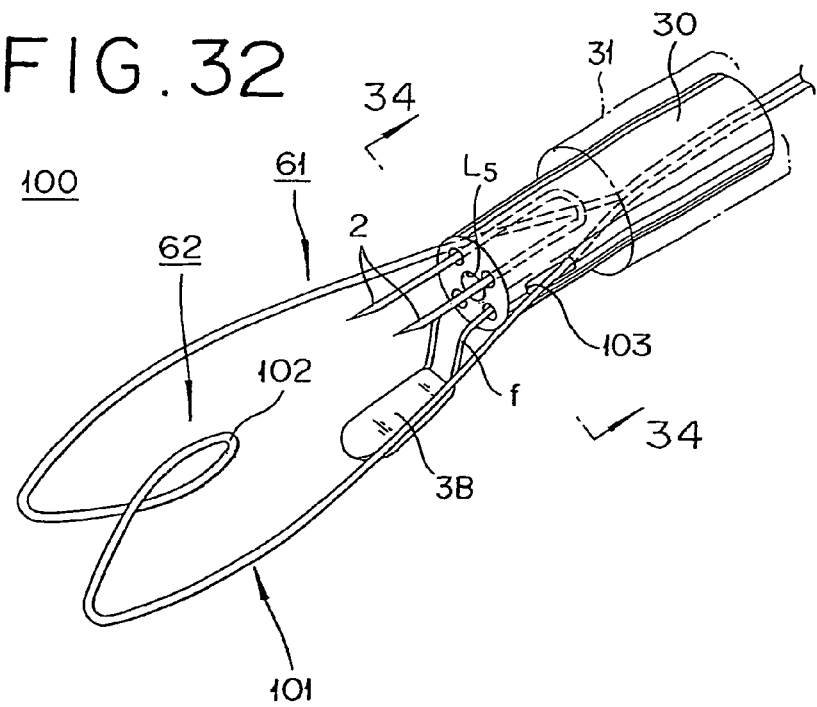
FIG. 32 is a schematic perspective view showing an eighth embodiment of the closing device.
Figure 33:
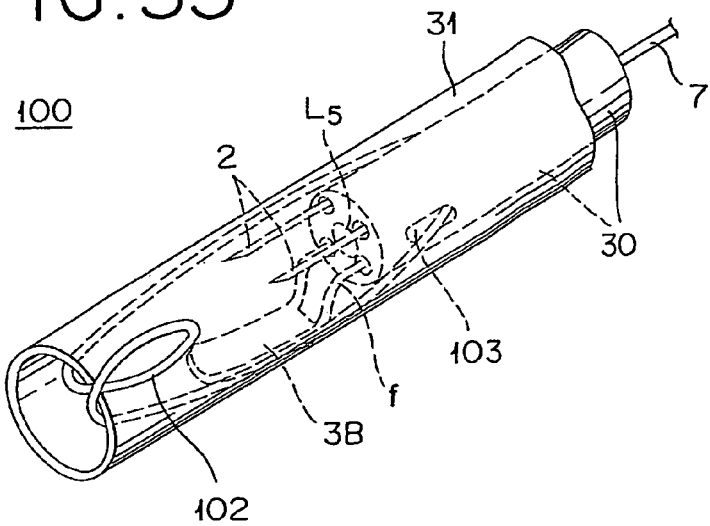
FIG. 33 is a schematic perspective view of the eight embodiment of the closing device showing the condition where a SP is caught.
Figure 34:
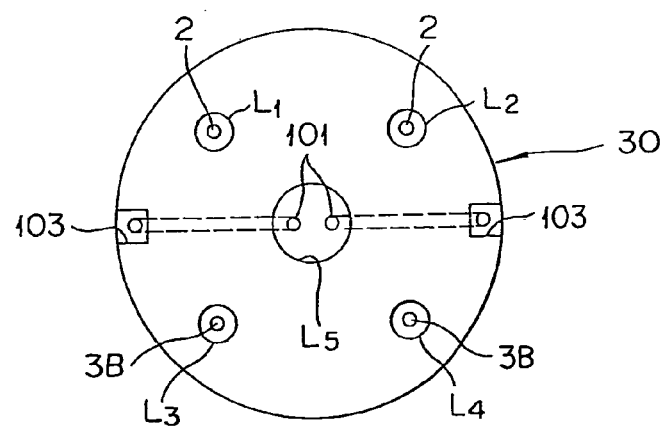
FIG. 34 is an end view of the device shown in FIG. 32 seen from the direction of the indicated by the line 34-34 in FIG. 32.

An eighth embodiment of the PFO closing device is shown in FIGS. 32-34. In the description which follows, features of this eighth embodiment of the closing device which are the same as those associated with embodiments described above are identified by the same reference numeral, and a detailed description of such features is not repeated.

The positioning and holding means 60, 80, 90 in the above-described embodiments are configured so that the SP M2 is held after positioning, and so that the positioning operation and the holding operation are to conducted sequentially. On the other hand, in this embodiment, the positioning operation and the holding operation can be conducted substantially concurrently at a stroke, and the configuration therefore is extremely simplified.

As shown in FIG. 32, the positioning and holding means 100 in this embodiment includes a positioning part 61 composed of a pair of elongated, comparatively long, elastic wire members 101 projecting in a fanned (diverging) manner from the distal end portion of a catheter 30, and a holding part 62 in which a projecting part 102 is centrally formed by deforming the distal end (tip) portions of the elastic wire members 101 into a substantially M-shaped form.

As shown in FIG. 34, the pair of elastic wire members 101 may be connected to the distal end of an operating member 7 passing through a central lumen L5, of a plurality of lumens L1-L5 formed in the catheter 30, or the two elastic members 101 themselves may pass through the central lumen L5, to be led to a hand-operated operating device provided at a base portion of the device. In any case, the proximal end (base) portions of the elastic wire members 101 extend along tapered grooves 103 formed in side portions of the outer periphery of the catheter 30. The tapered grooves 103 are configured to extend from the outer peripheral surface at side portions of the catheter 30 gradually toward the inside of the catheter (the grooves 103 are tapered or angled so that their depth is the smallest at the distal end portion of the grooves and increases gradually or in a tapering manner in the proximal direction). This allows the angle formed between the elastic wire members 101 to be set to a desired opening angle by regulating the inclination angle of the tapered grooves 103. Moreover, since the elastic wire members 101 are operated along the tapered grooves 103, the elastic wire members 101 can be relatively smoothly protruded from and retracted into the lumen L5 of the catheter 30, which promises good operationality.

The distal end (tip) portions of the elastic wire members 101 are bent comparatively sharply to the inner side, and are then directed to the proximal side at a central area, to obtain the roughly M-shaped overall form, and to form the projecting part 102. The projecting part 102 serves as a part for holding the SP M2 in relation to the puncturing direction of the needle part 2, from the back side.

As is clear from FIG. 1, in the case of holding the SP M2 from the back side, it is preferable to set the projecting part 102 in the state of being inclined against the plane formed by both the elastic wire members 101. In the positioning and holding means 100 in this embodiment, therefore, after the guiding catheter 31 is inserted into the left atrium L of the heart, the projecting part 102 is projected from an end portion of the guiding catheter 31, as shown in FIG. 33, so that the SP M2 can be relatively easily caught and held.

When the guiding catheter 30 is pulled into the right atrium R of the heart starting from the condition where the SP M2 is thus held by the projecting part 102, the elastic wire members 101 are pulled and developed into a fanned form, to make springy or elastic contact with the inner peripheral edge portion of the PFO 0, whereby the needle part 2 is positioned substantially in the center of the PFO 0. The projecting part 102 formed at the center of the elastic wire members 101 projects to the back side of the SP M2, namely, to the side of the left atrium of the heart, so as to hold the SP M2. While maintaining this holding condition, the catheter 30 is moved forwards, whereby the needle parts 2 puncture the SP M2. After the puncture, the elastic wire members 101 are moved forwards, and are moved from the side of the left atrium of the heart to the side of the right atrium of the heart. Then, the elastic wire members 101 are recovered into the tapered grooves 103 in the catheter 30, and the projecting part 102 is recovered into the lumen L5.

Then, in the condition where the needle part 2 and the clamping member 3B clamp the SS M1 and the SP M2 therebetween, an electric current is passed therebetween, whereby the tissues of the SS M1 and the SP M2 are fused together.

The positioning and holding means 100 in this embodiment is constructed so that the tip portions of the pair of elastic wire members 101 opened wider at a predetermined angle are deformed into the roughly M-shaped form. Therefore, it is quite simplified in construction and advantageous on a cost basis, as compared with at least some of the constructions described above in other embodiments.

The PFO closing device is not necessarily limited to the description set forth above and the above-described embodiments. For example, while the above embodiments are described as being used in a therapeutic procedure of closing a defect of PFO, the application of the closing device is not limited to this situation. For example, the device also has useful application to closing a passage-like defect, such as the case of a left atrial appendage.

In addition, while the PFO closing devices in the above embodiments are each stored in a catheter and the clamping means is operated through the operating member, this configuration is not limitative. For example, the PFO closing device can be combined with a so-called balloon catheter, to be fed to a predetermined position.

The principles, embodiments and operational characteristics of the closing device have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A patent foramen ovale closing device for bringing septum primum and septum secundum into contact with each other and joining them together, comprising:

a catheter dimensioned to be positioned in a living body and advanced into an atrium of a heart;

a needle part slidably positioned inside the catheter for puncturing the septum primum;

a clamping member mounted on the catheter and cooperable with the needle part to clamp, between the clamping member and the needle part, tissue of the septum primum and the septum secundum;

energy supplying means operatively connected to at least one of the needle part and the clamping member for supplying energy to join the tissue clamped between the needle part and the clamping member;

a main tube passing through the catheter and operable externally to axially move the main tube relative to the catheter;

an operating member extending through the main tube so as to be axially movable forwards and rearwards, the operating member protruding distally beyond a distal end of the main tube;

an intermediate sleeve body and a tip sleeve body positioned coaxially with respect to the operating member;

a contact member mounted at a distal end portion of the operating member to be brought into contact with the tip sleeve body upon axially moving the operating member, the contact member being positioned distally of the tip sleeve body and the intermediate sleeve body;

a first elastic wire member connecting the main tube and the intermediate sleeve body;

a second elastic wire member connecting the intermediate sleeve body and the tip sleeve body;

a third elastic wire member connecting the intermediate sleeve body and the tip sleeve body;

the first elastic wire member being deformed radially outwardly when the operating member is axially moved in a proximal direction so that the first elastic wire member makes elastic contact with an inner edge of the patent foramen ovale to position the needle part;

the second elastic wire member being curved by further axially moving the operating member in the proximal direction to thereby hold the septum primum by the tip sleeve body and the contact member; and the third elastic wire member curving outwardly during the axial movement of the operating member in the proximal direction to smooth out creases present in the septum primum.

2. The patent foramen ovale closing device as set forth in claim 1, wherein the catheter has a plurality of lumens, and the needle part and the clamping member pass through the lumens.

3. The patent foramen ovale closing device as set forth in claim 1, wherein the needle part comprises a plurality of spaced apart pointed wire members each having a circular cross-section and an outside diameter of 0.1 to 2 mm.

4. The patent foramen ovale closing device as set forth in claim 1, wherein the energy supplying means is a high-frequency monopolar system in which an electric current is passed between the needle part or the clamping member and a counter electrode plate is provided extracorporeally.

5. The patent foramen ovale closing device as set forth in claim 1, wherein the energy supplying means is a high-frequency bipolar system in which an electric current is passed between the needle part and the clamping member.

6. The patent foramen ovale closing device as set forth in claim 1, wherein the energy supplying means is a high-frequency bipolar system in which an electric current is passed by utilizing impedance of the tissue held between the needle part and the clamping member.

7. The patent foramen ovale closing device as set forth in claim 1, wherein the second elastic wire member is constructed to be more easily deformable than the first elastic wire member, and the third elastic wire member is projectingly deformable more easily than the second elastic wire member.

8. The patent foramen ovale closing device as set forth in claim 1, wherein the contact member mounted at a distal end portion of the operating member is an enlarged distal end portion of the operating member.

9. The patent foramen ovale closing device as set forth in claim 1, wherein the clamping member has a distal end portion in which a generally U-shaped wire member is covered with a plate member made of a conductive material.

10. The patent foramen ovale closing device as set forth in claim 1, wherein the clamping member includes two spaced apart wires each provided with a bent portion.

* * * * *